US007659087B2

(12) United States Patent
Colgin et al.

(10) Patent No.: US 7,659,087 B2
(45) Date of Patent: Feb. 9, 2010

(54) METHODS AND DEVICES FOR DIAGNOSIS OF APPENDICITIS

(75) Inventors: Mark A. Colgin, Castle Rock, CO (US); John F. Bealer, Englewood, CO (US); Richard G. Donnelly, Fort Collins, CO (US)

(73) Assignee: AspenBio Pharma, Inc., Castle Rock, CO (US)

( * ) Notice: Subject to any disclaimer, the term of this patent is extended or adjusted under 35 U.S.C. 154(b) by 0 days.

(21) Appl. No.: 11/670,882

(22) Filed: Feb. 2, 2007

(65) Prior Publication Data
US 2007/0249003 A1    Oct. 25, 2007

Related U.S. Application Data

(63) Continuation-in-part of application No. 11/189,120, filed on Jul. 25, 2005.

(60) Provisional application No. 60/590,631, filed on Jul. 23, 2004.

(51) Int. Cl.
G01N 33/00 (2006.01)
G01N 33/53 (2006.01)
C12Q 1/00 (2006.01)

(52) U.S. Cl. .......................... 435/7.92; 435/7.1; 435/4

(58) Field of Classification Search .................. None
See application file for complete search history.

(56) References Cited

U.S. PATENT DOCUMENTS

| 4,493,795 | A | 1/1985 | Nester, Jr. et al. |
| 4,833,074 | A | 5/1989 | Fagerhol et al. |
| 5,055,389 | A | 10/1991 | Bar-or et al. |
| 5,350,687 | A | 9/1994 | Odink et al. |
| 5,455,160 | A | 10/1995 | Fagerhol et al. |
| 5,470,750 | A | 11/1995 | Bar-Or |
| 5,552,295 | A | 9/1996 | Stanker et al. |
| 5,702,920 | A | 12/1997 | Odink et al. |
| 6,451,550 | B1 | 9/2002 | Eckersall |
| 6,749,565 | B2 | 6/2004 | Chundner |
| 2003/0224452 | A1 | 12/2003 | Colgin et al. |
| 2004/0121343 | A1 | 6/2004 | Buechler et al. |
| 2004/0175754 | A1 | 9/2004 | Bar-Or et al. |
| 2004/0241775 | A1 | 12/2004 | Romero et al. |

(Continued)

FOREIGN PATENT DOCUMENTS

EP    EP 0263072    4/1988

(Continued)

OTHER PUBLICATIONS

Yui et al., Biol Pharm Bull. Jun. 2003;26(6):753-760.*

(Continued)

Primary Examiner—Cherie M Woodward
(74) Attorney, Agent, or Firm—Greenlee, Winner and Sullivan, P.C.

(57) ABSTRACT

A method is provided for determining the severity of appendicitis in a patient that includes testing a blood, serum or plasma sample from the patient for the quantity of MRP8/14 in the sample and comparing it with the quantity of MRP8/14 present in standard samples correlated with an appendicitis severity scoring system. A histologically-based appendicitis severity scoring system is also provided. Immunoassays and kits for performing the appendicitis assays of this invention are also provided, as are standard samples and data correlating MRP8/14 quantities present in patient samples to histologically-based appendicitis severity grades. The methods and immunoassay devices and kits of this invention are useful for managing the treatment of patients presenting with appendicitis symptoms.

24 Claims, 9 Drawing Sheets

U.S. PATENT DOCUMENTS

2005/0095249 A1   5/2005   Hanash
2009/0155813 A1   6/2009   Colgin et al.

FOREIGN PATENT DOCUMENTS

| EP | 0 428 080 | 5/1991 |
|---|---|---|
| EP | 058201 | 3/1994 |
| WO | WO 98/35985 | 8/1998 |
| WO | WO 00/26668 | 5/2000 |
| WO | WO 03/069349 | 8/2003 |
| WO | WO 2004/032711 | 4/2004 |
| WO | WO 2004/057341 | 7/2004 |
| WO | WO 2004/059293 | 7/2004 |
| WO | WO2006/012588 | 2/2006 |

OTHER PUBLICATIONS

Power et al., Br J Surg. Apr. 2005;92(Suppl 1):97-98.*
FDA Guidance—Class II Special Controls Guidance Document: Fecal Calprotectin Immunological Test Systems, issued on Jul. 27, 2006.*
APPYSCORE Trademark SN 7704421 (2006).*
Birchley, D. (2006) "Patients with Clinical Acute Appendicitis Should Have Pre-Operative Full Blood Count and C-Reactive Protein Assays," *Ann. R. Coll. Surg. Engl.* 88:27-32.
Maruniak et al. (1987) "Acute Phase Reactants in Inflammatory Conditions of the Colon Relationship with Nerve Hypertrophy," *Fed. Proc.* 46(3):986, Abstract No. 3900.
Sack et al. (2006) "Diagnostic Value of Blood Inflammatory Markers for Detection of Acute Appendicitis in Children," *BMC Surg.* 6:15.
Supplementary Partial European Search Report, Corresponding to European Application No. 05 77 5574, Completed on Jan. 14, 2008.
Yang et al. (2006) "Laboratory Tests in Patients with Acute Appendicitis," *ANZ J. Surg.* 76:71-74.
Cell Sciences. Human Calprotectin ELISA Kit. 2006, IN: Cell Sciences, Inc. datasheet. Retrieved online at <<URL: http://www.cellsciences.com/content/p-detail.asp?rowid=8403>>.
Cell Sciences. Anti-human S100A8.A9 (MPR-8/MPR-14), Calprotectin, Clone 27E10, Monoclonal Antibody. 2006, IN: Cell Sciences Inc. datasheet. Retrieved online at <<URL: http://www.cellsciences.com/content/p-detail.asp?rowid=7581>>.
Aadland et al. (2002) "Faecal Calprotectin: A Marker of Inflammation Throughout the Intestinal Tract," *Eur. J. Gasroenterol Hepatol.* 14:1823-825.
Ahlquist et al. (1996) "Stool Markers for Colorectal Screening: Future Considerations,"*Dig. Dis.* 14(3):132-144.
Alic, M. (1999) "Is Fecal Calprotectin the next Standard in Inflammatory Bowel Disease Activity Test," (letter) *Am. J. Gastroenterol.* 94(11):3370-3371.
Arnott et al. (2002) "Review Article: Is Clinical Remission the Optimum Therapeutic Goal in the Treatment of Crohn's Disease," *Aliment Pharmacol. Ther.* 16:857-867.
Arredouani et al. (2005) "Haptoglobin Dampnes Endotoxin-Induced Inflammatory Effects Both In Vitro and In Vivo, " *Immunology* 114(2):263-271.
Avrameas et al. (1978) "Coupling of Enzymes to Antibodies and Antigens, " *Scand. J. Immunol.* 8(7):7-23.
Barcia et al. (Dec. 2002) "Neutrophil Count in Normal Appendix and Early Appendicitis: Diagonstic Index of Real Acute Inflammation," *Ann. Diag. Path.* 6(6):352-356.
Berger et al. (1997) "Time-Scale of Interleukin-6, Myeloid Related proteins (MRP), C Reactive Protein (CRP, and Endotoxin Plasma Levels During the Postoperative Acute Phase Reaction," *Shock* 7(6):422-426.
Berntzen et al. (1991) "Calprotectin (The L1 Protein) During Surgery in Patients with Rheumatoid Arthritis," *Scand. J. Clin. Lab. Invest.* 51(7):643-650.
Berntzen et al. (1991) "The L1 Protein as a New Indicator of Inflammatory Activity in Patients with Juvenile Rheumatoid Arthritis," *J. Rheumatol.* 18(1):133-138.

Berntzen et al. (1989) "A Longitudinal Study of the Leukocyte Protein L1 as an Indicator of Disease Activity in Patients with Rheumatoid Arthritis," *J. Pheumatol.* 16(11):1416-1420.
Berntzen et al. (1988) "The Major Leukocyte Protein L1 as an Indicator of Inflammatory Joint Disease," *Scand. J. Rheumatol.* Supp 76:251-256.
Berntzen et al. (1991) "The Leukocyte Protein L1 in Plasma and ynovial Fluid from Patients with Rheumatoid Arthritis and Osteoarthritis," *Scand J. Rheumatol.* 20(2):74-82.
Berstad et al. (2000) "Relationship Between Intestinal Permeability and Calprotectin in Gut Lavage Fluid," *Scand J. Gastroenterol.* 35(1):64-69.
Bjarnason et al. (2001) "Fecal Calprotectin: A Significant Step in the Noninvasive Assessment of Intestinal Inflammation," *J. Pediat. Gastroent.Nutr.* 33:11-13.
Bjerke et al. (1993) "Distribution of Macrophages and Granulocytes Expressing L1 Protein (Calprotectin) in Human Peyer's Patches Compared with Normal Ileal Lamina Propria and Mesenteric Lymph Nodes," *Gut* 34(10):1357-1363.
Bogumil et al. (1998) "Serum Levels of Macrophage-Derived Protein MRP8/14 are Elevated in Active Multiple Sclrosis," *Neurosci. Lett.* 247(2-3):195-197.
Bonaldo et al. (1996) "Normalization and Subtraction: Two Approaches to facilitate Gene Discovery," *Genmome Res.* 6:791-806.
Brandtzaeg et al. (1987) "Distribution of a Formalin-Resistant Myelomonocytic Antigen (I1) in Human Tissues. I. Comparison with Other Leukocyte Markers by Paired Immunofluorescence and Immunoenzyme Staining," *Am. J. CLin. Pathol.* 87(6):681-699.
Brandtzaeg et al. (1987) "Distribution of a Formalin-Resistant Myelomonocytic Antigen (I1) in Human Tissues. II. Normal and Aberrant Occurrence in Various Epithelia," *Am. J. Clin. Pathol.* 87(6):700-707.
Brantzaeg et al. (1992) "The Leucocyte Protein L1 (Calprotectin): Usefulness as an Immunohistochemical Marker Antigen and Putative Biological Function," *Histopathol.* 21(2):191-196.
Brun et al. (1994) "Sjögren's Syndrom in Inflammatory Rheumatic Disease: Analysis of the Leukocyte Protein Calprotectin in Plasma and Saliva," *Scand. J. Rheumatol.* 23(3):114-118.
Brun et al. (1992) "Calprotectin in Patients with Rheumatoid Arthiritis: Relation to Clinical and Laborotory Variables of Disease Activity," *J. Rheumatol.* 19(6):859-862.
Brydon et al. (2001) "Faecal Calprotectin Levels and Colorectal Neoplasia," *Gut* 48(4):579-580.
Bunn et al. (2001) "Fecal Calprotecin as a Measure of Disease Activity in Childhood Inflammatory Bowel Disease," *J. Pediat. Gastroenterol. Nutr.* 32(2):171-177.
Bunn et al. (2001) "Fecal Calprotectin: Validation as a Nonivasive Measure of Bowel Inflammation in Childhood Inflammatory Bowel Disease," *J. Pediat. Gastroenterol. Nutr.* 33(1):14-22.
Burkhardt et al. (2001) "An Increase in Myeloid-Related Protein Serum Levels Precedes Acute Renal Allograft Rejection," *J. Am. Soc. Nephrol.* 12:1947-1957.
Clark et al. (1990) "Calgranulin Expression and Association with the Keratinocyte Cytoskeleton," *J. Pathol.* 160(1):25-30.
Cunliffe, R.N. (2003) "α-Defensins in the Gastrointestinal Tract," *Mol. Immunol.* 40:463-467.
Cunliffe et al. (2004) "Expression and Regulation of Antimicrobial Peptides in the Gastrointestinal Tract," *J. Leuk. Biol.* 75:49-58.
Dale et al. (1985) "Distribution of a New Myelomonocytic Antigen (L1) in Human Peripheral Blood Leulocytes. Immunofluorescence and Immunoperoxidase Staining Features in Caomparison with Lysozyme and Lactoferrin," *Am. J. Clin. Pathol.* 84(1):24-34.
Dale et al. (1989) "Expression of the Epithelial L1 Antigen as an Immunohistochemical Marker or Squamous Cell Carcinoma of the Lung," *Histopathology* 14(5):493-502.
Dale, I. (1990) "Plasma Levels of the Calcium-Binding L1 Leukocyte Protein: Standardization of Blood Collection and Evaluation of Reference Intervals in Healthy Controls," *Scand. J. Clin. Lab. Invest.* 50(8):837-841.
Deichmann et al. (2001) "The Protein Phosphatase 2A Subunit Bg Gene is Identified to be Differentially Expressed in Malignant Melanomas by Subtractive Suppression Hybridization," *Melanoma Res.* 11(6):577-585.

DeLuca (1982) "Immunofluorescence Analysis," In; *Antibody as a Tool*, Marchalonis et al. Eds., John Wiley and Sons, Ltd., pp. 189-231.

Dorbryszycka, W. (1997) "Biological Functions of Haptoglobin—New Pieces to an Old Puzzle," *Eur. J. Clin. Chem. Clin. Biochem.* 35(9):647-654.

Eversole et al. (1993) "Keratinocyte Expression of Calprotectin in Oral Inflammatory Mucosal Disease," *J. Oral.. Pathol. Med.* 22(7):303-307.

Eversole et al. (1992) "The Distribution of the Antimicrobial Protein, Calprotectin, in Normal Oral Keratinocytes," *Arch. Oral. Biol.* 37(11):963-968.

Fagerhol et al. (1990) "Calprotectin (The L1 Leukocyte Protein)," In; *Stimulus Response Coupling. The Role of Intracellular Calcium-Binding Proteins*, Smith et al. Eds., CRC Press, Boca Raton, Fl., USA, pp. 187-210.

Flagerhol, M.K. (2000) "Calprotectin, a Faecal Marker of Organic Gastrointestinal Abnormality," *Lancet* 356(9244):1783-1784.

Flum et al. (2001) "Has Misdiagnosis of Appendicitis Decreased over Time? A Population-Based Analysis," *JAMA* 286(14):1748-1753.

Foell et al. (2003) "Neutrophil Derived Human S100A12 (EN-RAGE) is Strongly Expressed During Chronic Active Inflammatory Bowel Disease," *Gut* 52:847-853.

Fosse et al. (1994) "Reduced Complement and Granulocyte Activation with Heparin-Coated Cardiopulmonary Bypass," *Ann. Thoracic Surg.* 58(2):472-477.

Frosch et al. (2000) "Myloid-Related Proteins 8 and 14 are Specifically Secreted During Interaction of Phagocytes and Activated Endothelium and are Useful Markers for Monitoring Disease Activity in Pauciarticular-Onset Juvenile Rheumatoid Arthritis," *Arthritis Rheum.* 43:628-637.

Gabrielsen et al. (1986) "Epidermal and Dermal Distribution of a Myelomonocytic Antigen (L1) Shared by Epithilial Cells in Various Inflammatory Skin Disease," *J. Am. Acad. Dermatol.* 15(2 pt 1):173-179.

Gabrielsen et al. (1988) "Epithelial Distribution of a Myelomonocytic Antigen L1 in Relation to Cutaneous Melignancies and Melanocytic Naevi," *Br. J. Dermatol.* 118(1):59-67.

Galfre et al. (1981) "Preparation of Monoclonal Antibodies: Strategies and Procedures," *Meth. Enzymol.* 73:3-46.

Garred et al. (1993) "Calprotectin and Complement Activation During Major Operations With or Without Cardiopulmonary Bypass," *Ann. Thoracic Surg.* 55(3):694-699.

Gasché, C. (2005) "Laboratory Tests—What do They Tell Us," Falk Symposium Abstract, Jun. 17-18, 2005, Munich, Germany.

Gaya et al. (2002) Faecal Calprotectin: A Bright Future for Assessing Disease Activity in Crohn's Disease, *Q. J. Med.* 95:557-558.

Giampalmo et al. (1983) "Enzymatic Activation of Lymphoid Population Following Inflammatory Reactions in the Human Appendix," *Z Mikrosk Anat Forsch* 97(5):785-796 Abstract Only.

Gilbert et al. (1996) "Fecal Marker Variability in Colorectal Cancer: Calprotectin Versus Hemoglobin," *J. Gastroenterol.* 31(10):1001-1005.

Golden et al. (1996) "Calprotectin as a Marker of Inflammation in Cystic Fibrosis," *Arch. Dis. Childhood* 74(2):136-139.

Haga et al. (1993) "Calprotectin in Patients with Systemic Lupus Erythematosus: Relation to Clinical and Laboratory Parameters of Disease Activity," *Lupus* 2(1):47-50.

Haidekker et al. (2002) "A Novel Approach to Blood Plasma Viscosity Mesurement Using Fluorescent Molecular Rotors," *Am. J. Physiol. Heart Circ. Physio.* 282:H1609-1614.

Hammer et al. (1995) "A Longitudinal Study of Calprotectin as an Inflammatory Marker in Patients with Reactive Arthritis," *Clin. Exp. Rheumatol.* 13(1):59-64.

Hanai et al. (2003) "Clinical Significance of Faecal Calprotectin Levels in Patients with Ulcerative Colitis," *Nippon Shokakibyo Gakkai Zasshi* 100:21-27.

Harkness, J. (1963) "A New Method for the Measurement of Plasma Viscosity," *Lancet* 2:280-281.

Hessian et al. (2001) "The Heterodimeric Complex of MRP-8 (S100A8) and MRP-14 (S100A9): Antibody Recognition, Epitope Definition and the Implications for Structure," *Eur. J. Biochem.* 268:353-363.

Hessian et al. (Feb. 1993) "MRP-8 and MRP-14, Two Abundant Ca2+-Binding Proteins of Neutrophils and Monocytes," *J. Leuk Biol.* 53:197-204.

Hetland et al. (1992) "Levels of Calprotectin (leukocyte L1 Protein) During Apheresis," *Scand. J. CLin. Lab. Invest.* 52(6):479-482.

Homann et al. (1995) "Plasma Calprotectin: A New Prognostic Marker of Survival in Alchohol-Induced Cirrhosis," *Hapatol.* 21(4):979-985.

Hsieh et al. (2004) "S100 Protein Translocation in Response to Extracellular S100 is Mediated by Receptor for Advanced Glycation Endproducts in Humna Endothelial Cells," *Biochm. Biophys. Res. Commun.* 316:949-959.

Ikemoto et al. (2003) "New ELISA System for Myeloid-Related Protein Complex (MRP8/14) and its Clinical Significance as a Sensitive Marker for Inflammatory Responses Associated with Transplant Rejection," *Clin. Chem.* 49:594-600.

Johne et al. (1997) "Functional and Clinical Aspects of the Myelomonocyte Protein Calprotectin," *Mol. Pathol.* 50(3):113-123.

Johne et al. (2001) "A New Fecal Calprotectin Test for Colorectal Neoplasia. Clinical Results and Comparison with Previous Method," *Scand. J. Gastroenterol.* 36(3):291-296.

Katnik et al. (1989) "Monoclonal ANtibodes Against Human Haptoglobin," *Hybridoma* 8(5):551-560.

Kelly et al. (1991) "Morphological Evidence for Calcium-Dependent Association of Calgranulin with the Epdermal Cytoskeleton in Inflammatory Dermatoses," *Br. J. Dermatol.* 124(5):403-409.

Kelly et al. (1989) "Calgranulin Expression in Inflammatory Dermatoses," *J. Pathol.* 159(1):17-21.

Kerkhoff et al. (1998) "Novel Insights into Structure and Function of MRP8 (S100A8) and MRP14 (S100A9)," *Biochim.I Biophys. Acta* 1448(2):200-211.

Kjeldsen-Kragh et al. (1995) "Changes in Laboratory Variable in Rheumatoid Arthritis Patients During a Trial of Fasting and One-Year Vegetarian Diet," *Scand. J. Rheumatol.* 24(2):85-93.

Koike et al. (1998) "Intracellular Localization of Migration Inhibitory Factor-Related Protein (MRP) and Detection of Cell Surface MRP Binding Sites on Human Leukemia Cell Lines," *J. Biochem.* 123(6):1079-1087.

Kristinsson et al. (1998) "Fecal Excretion of Calprotectin Concentration in Patients with Colorectal Carcinoma," *Dos. Colon Rectum* 41(3):316-321.

Kristinsson et al. (2001) "Fecal Ecretion of Calprotectin in Colorectal Cancer; Relationship to Tumor Characteristics," *Scand. J. Gastroenterol* 36(2):202-207.

Kronborg et al. (2000) "Faecal Calprotectin Levels in a High Risk Population for Colorectal Neoplasia," *Gut* 46(6):795-800.

Kumar et al. (2001) "Dimeric S100A8 in Human Neutrophils is Diminished After Phagocytosis," *J. Leukoc. Biol.* 70(1):59-64.

Limburg et al. (2000) "Fecal Calprotectin Levels Predict Colorectal Inflammation Among Patients with hronic Diarrhea Referred for Colonoscopy," *Am. J. Gastroenterol* 95(10):2831-2837.

Longbottom et al. (1992) "Subunit Structure of Calgranulins A and B Obtained from Sputum, Plasma, Granulocytes and Cultures Epithelial Cells," *Biochim. Biophys. Acta* 1120(2):215-222.

Lugering et al. (1995) "The Myeloic Related Protein MRP8/14 (27E10 Antigen)-Usefulness as a Potential Marker for DIsese Activity in Ulcerative Colitis and Putative Biological Function," *Eur. J. Clin. Invest.* 25(9):659-664.

Meling et al. (1996) "Faecal Calprotectin Shedding After Short-Term Treatment with Non-Steroidal Anti-Inflammatory Drugs," *Scand. J. J. Gastroenterology* 31(4):339-34.

Moen et al. (1994) "Roller and Centrifugal Pumps Compared in Vitro with Regard to Haemolysis, Granulocyte and Complement Activation," *Perfusion* 9(2):109-117.

Muller et al. (1994) "Elevated Serum Calprotectin Levels in HIV-Infected Patients: The Calprotectin Response During ZDV Treatment is Associated with Clinical Events," *J. Acq. Immun. Def. Syndr.* 7(9):931-939.

Neary, W. (2001) Misdiagnosis of Appendicitis Continues Despite New Tools, Press Release from University of Washington.

Ng et al. (Feb. 2002) "Clinical Analysis of the Related Factors in Acute Appendicitis," *Yale J. Biol. Med.* 75:41-45.

Olafsdottir et al. (2002) "Faecal Calprotectin in Infants with Infantile Colic, Healthy Infants, Children with Inflammatory Bowel Disease, Children with Recurrent Abdominal Pain and Healthy Children," *Acta Paediatr.* 91:45-50.

Power et al. (2005) "Raised Faecal Calprotectin Levels in Patients Presenting with Right Iliac Fossa Pain Warrant Mandatory Laparoscopy: A Non-Invasive Predictor of Acute Appendicitis," *Thieme Connect, Endoscopyl* 37:DOI:10.1055/2-2005-868524.

Power et al. (2004) "Raised Faecal Calprotecting Levels in Patients Presenting With Right Iliac Fossa Pain Warrant Mandatory Laparoscopy: A Non-Invasive Predictor of Acture Appendicitis," Irish Society of Gastroenterology Winter Meeting Program, Oral Presentation.

Riviera-Chavez et al. (Mar. 2003) "Reginal and Systemic Cytokine Responses to Acute Inflammation of the Veriform Appendix," *Ann. Surg.* 237(3):408-416.

Robinson et al. (2002) "The S100 Family Heterodimer, MRP8/14, Binds with High Affinity to Heparin and Heparan Sulfate Glycosaminoglycans on Endothelial Cells," *J. Biol. Chem.* 277:3658-3665.

Rodwell et al. (1984) "Linker Technology: Antibody-Mediated Delivery Systems," *Biotech.* 3:889-894.

Roseth et al. (Oct. 2004) "Normalization of Faecal Calprotectin: A Predictor of Mucosal Healing in Patients with Inflammatory Bowel Disease," *Scand. J. Gastroenterol.* 39(10):1017-1020.

Roseth et al. (1992) "Assessment of the neutrophil Dominating Protein Calprotectin in Feces. A Methodologic Study," *Scand. J. Gastroenterol.* 27(9):793-798.

Roseth et al. (1993) "Faecal Calprotectin: A Novel Test for the Diagnosis of Colorectal Cancer," *Scand J. Gastroenterol.* 28(12):1073-1076.

Roseth et al. (1997) "Assessment of Disease Activity in Ulcerative Colitis by Faecal Calprotectin, A Novel Granulocyte Marker Protein," *Digestion* 58(2):176-180.

Roseth et al. (1999) "Correlation Between Feacal Excretion of indium-111-labelled Granulocytes and Calprotectin, a Granulocyte Marker Protein, in Patients with Inflammatory Bowel Disease," *Scand. J. Gastroenterol.* 34(1):50-54.

Rychman et al. (2003) "Proinflammatory Activities of S100: Proteins S100A8, S100A9, and S100A8/A9 Induce Neutrophil Chemotaxis and Adhesion," *J. Immunol.* 170:3233-3242.

Saintigny et al. (1992) "Differential Expression of Calgranulin A and B in Various Epithelial Cell Lines and Reconstructed Epidermis," *J. Invest. Dermatol.* 99(5):639-644.

Sander et al. (1984) "Plasma Levels of the Leucocyte L1 Protein in Febrile Conditions: Relation to Aetiology, Number of Leucocytes in Blood, Blood Sedimentation Reaction and C-Reactive Protein," *Scand. J. Clin. Lab. Invest.* 44(4):357-362.

Semb et al. (1991) "Cardiac Surgery and Distribution of the Leukocyte L1 Protein-Calprotectin," *Eur. J. Cardio-Thoracic Surg.* 5(7):363-367.

Shanahan, F. (2001) "Inflammatory Bowel Disease Immunodiagnostics, Immunotherapeutics, andd Ecotherapeutics," *Gastroenterol.* 120:622-635.

Stockley et al. (1984) "Relationship of Neutrophil Cytoplasmic Protein (I1) to Acute and Chronic Lung Disease," *Scand. J. CLin. Lab. Invest.* 44(7):629-634.

Striz et al. (2004) "Calprotectin—A Pleiotropic Molecule in Acute and Chronic Inflammation," *Physiol. Res.* 53:245-253.

Thomas et al. (2000) "Assessment of Ileal Pouch Inflammation by Single-Stool Calprotectin Assay," *Dis. Colon Rectum* 43(2):214-220.

Tibble et al. (2000) "A Simple Method for Assessing Intestinal Inflammation in Crohn's Disease," *Gut* 47(4):506-513.

Tibble et al. (2001) "Faecal Calprotectin and aecal Occult Blood Tests in the Diagnosis of Colorectal Carcinoma and Adenoma," *Gut* 49:402-408.

Tibble et al. (2001) "Markers of Intestinal Inflammation and Predictors of Clinical Relapse in Patients with Quiescent IBD," *Medscape Gastroenterol.* 3(2):1-4.

Tibble et al. (2000) "Surrogate Markers of Intestinal Inflammation are Predictive of Relapse in Patients with Inflammatory Bowel Disease," *Gastroentology* 119(1):15-22..

Tibble et al. (1999) "High Prevalence of NSAID Enteropathy as Shown by a Simple Faecal Test," *Gut* 45(3):362-363.

Ton et al. (2000) "Improved Assay for Fecal Calprotectin," *Clinica Chimica Acta* 292(1-2):41-54.

Tungekar et al. (1991) "The L1 Antigen and Squamous Metaplasia in the Bladder," *Histopathol* 19(3):245-250 .

Waraich et al. (Mar. 1997) "The Accessory Cell Populations in Ulcerative Colitis: A Comparison Between the Colon and Appendix in Colitis and Acute Appendicitis," *Hum. Pathol.* 28(3):297-303 Abstract Only.

Wehkamp et al. (2005) "Human Defensins in Crohn's Disease. A Molecular Link to Mucosal Barrier Dysfunction," *Chem. Immunol. Allergy* 86:42-54.

Wilkinson et al. (1988) "Expression Pattern of Two Related Cystic Fibrosis-Associated Calcium Binding Proteins in Normal and Abnormal Tissues," *J. Cell. Sci.* 91(2):221-230.

Ye et al. (2003) "Haptoglobin-Alpha as PotentialSerum Biomarker in Ovarian Cancer: Identification asnCharacterization Using Proteomic Profiling and Mass Spectometry," *Clin Cancer Res.* 9(8):2904-2911.

Yerly et al. (1990) "Development of a Haptoglobin ELISA. Its Use as an Indicator for Malaria," *Acta Trop.* 47(4):237-244.

Zwaldo et al. (1986) "A Monoclonal Antibody to a Subset of Human Monocytes Found Only in the Peripheral Blood and Inflammatory Tissues," *J. Immunol.* 137(2):512-518.

Avrameas et al. (1978) "Coupling of Enzymes to Antibodies and Antigens," *Scand. J. lmmunol.* 8(7):7-23.

Bhardwaj, R.S. (1992) "The Calcium-Binding Proteins MRP8 and MRP14 form a Membrane-Associated Heterodimer in a Subset of Monocytes/Macrophages Present in Acute but Absent in Chronic Inflammatory Lesions," *Eur. J. lmmunol.* 22(7):1891-1897.

DeLuca (1982) "Immunofluorescence Analysis," In; *Antibody as a Tool*, Marchalonis et al. Eds., John Wiley and Sons, Ltd., pp. 189-231.

Foell et al. (2003) "Neutrophil Derived Human S100A12 (EN-RAGE) is Strongly Expressed During Chronic Active Inflammatory Bowel Disease,"*Gut* 52:847-853.

Gaya DR, Mackenzie JF. Faecal calprotectin: a bright future for assessing disease activity in Crohn 's disease. Q J Med 2002; 95:557 (editorial).

Hessian et al. (Feb. 1993) "MRP-8 and MRP-14, Two Abundant Ca2+-Binding Proteins of Neutrophils and Monocytes," *J. Leuk Biol.* 53:197-204.

Lagasse E and Clerc RG, Mol Cell Biol. Jun. 1988; 8(6): 2402-2410.

Maeda N, J Biol Chem. Jun 10, 1985;260(11):6698-709.

Moen O, Fosse E, Braten J, Andersson C, Fagerhol MK, Venge P, Hogasen K, Mollnes TE. Roller and centrifugal pumps compared in vitro with regard to haemolysis, granulocyte and complement activation. Perfusion 1994; 9(2):109-17.

Pekna M, Borowiec J, Fagerhol MK, Venge P, Thelin S. Biocompatibility of heparin-coated circuits used in cardiopulmonary bypass. Scand J Thorac Cardiovasc Surg 1994; 28(1):5-11.

Que et al. (2004) "Myeloid-Related Protein (MRP)8/14 (Calprotectin) and its Subunits MRP8 and MRP14 in Plaque-Induced Early Gingival Inflammation," *J. Clin. Peridon.* 31(11):978-984.

Roth, J. et al., "Expression of the calcium-binding proteins MRP8 and MRP14 in monocytes is regulated by a calcium-induced suppressor mechanism," Biochem. J. (1994) 301, 655-660.

Rypins et al. (2002) "$^{99m}$Tc Anti-CD 15 Monoclonal Antibody (LeuTech) Imaging Improves Diagnostic Accuracy and Clinical Management in Patients with Equivocal Presentation of Appendicitis," *Ann. Surg.* 235(2):232-239.

Tibble, J. A. et al. (2001) "Fecal Calprotectin as an Index of Intestinal Inflammation," Drugs of Today 37(2):85-96.

Tibble, J. A. et al. (2001) "Non-Invasive Investigation of Inflammatory Bowel Disease," World J. Gastroenterol. 7(4):460-465.

Yildirim et al. (2006) "The Role of Serum Inflammatory Markers in Acute Appendicitis and Their Success in Preventing Negative Laparotomy," *J. Invest. Surg.* 19:345-352.

Yoon et al. (Dec. 2002) "Human Cytokine Levels in Nonperforated Versus Perforated Appendicitis: Milecular Serum Markers for Extent of Disease," *Am. Surg.* 68(12):1033-1037.

Webpage information from internet at www.fda.gov/cder/drug/advisory/technetium99.htm, source material indicated as from Dec. 19, 2005.

Webpage information from internet at www.palatin.com/neutrospecstatement.asp and at www.palatin.com/news/news.asp?ID=134 and , source material indicated as from Dec. 19, 2005.

Birchley, D. (2006) "Patients with Clinical Acute Appendicitis Should Have Pre-Operative Full Blood Count and C-Reactive Protein Assays," *Ann. R. Coll. Surg. Engl.* 88:27-32.

Maruniak et al. (1987) "Acute Phase Reactants in Inflammatory Conditions of the Colon Relationship with Nerve Hypertrophy," *Fed. Proc.* 46(3):986, Abstract No. 3900.

Sack et al. (2006) "Diagnostic Value of Blood Inflammatory Markers for Detection of Acute Appendicitis in Children," *BMC Surg.* 6:15.

Supplementary Partial European Search Report, Corresponding to European Application No. 05 77 5574, Completed on Jan. 14, 2008.

Yang et al. (2006) "Laboratory Tests in Patients with Acute Appendicitis," *ANZ J. Surg.* 76:71-74.

GenBank Accession No. NP005134, Oct. 23, 2005.

GenBank Accession No. P06702, Sep. 13, 2005.

Hycult Biotechnology b.v., "Monoclonal Antibody to Human S100A8/A9 (MRP-8/MRP-14)," Calprotectin Clone 27E10 Information Sheet, Catalog No. HM2156 (2005).

Hycult Biotechnology b.v., "ELISA Test Kit for Human Calprotectin," Information Sheet, Catalog No. HK325 (2005).

N. Lugering, et al. (1995), "Serum 27E10 antigen: a new potential marker for staging HIV disease," *Clin. Exp. Immunol.* 101:249-253.

English translation of Japanese Official Action for corresponding Japanese Patent Application No. 2007-522830 (Atty Ref. 65-04 JP), dated Sep. 29, 2009 (mailed Oct. 1, 2009).

English translation of Japanese Official Action for corresponding Japanese Patent Application No. 2009-153020 (Atty Ref. 65-04 JP1), dated Nov. 16, 2009 (mailed Nov. 18, 2009).

* cited by examiner

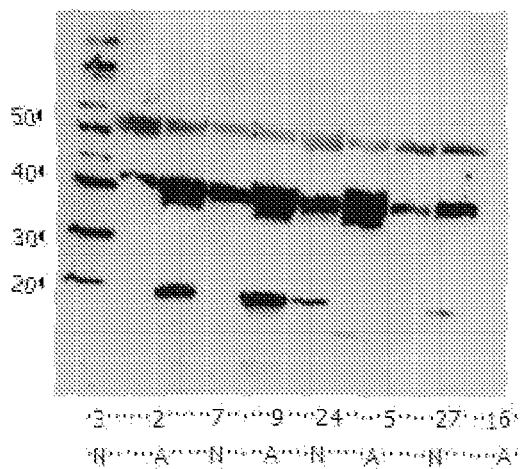 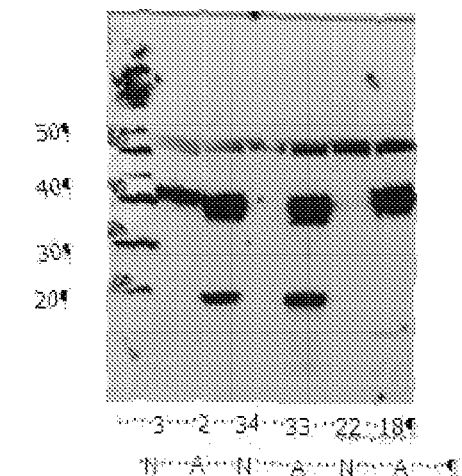
FIGURE 7A          FIGURE 7B
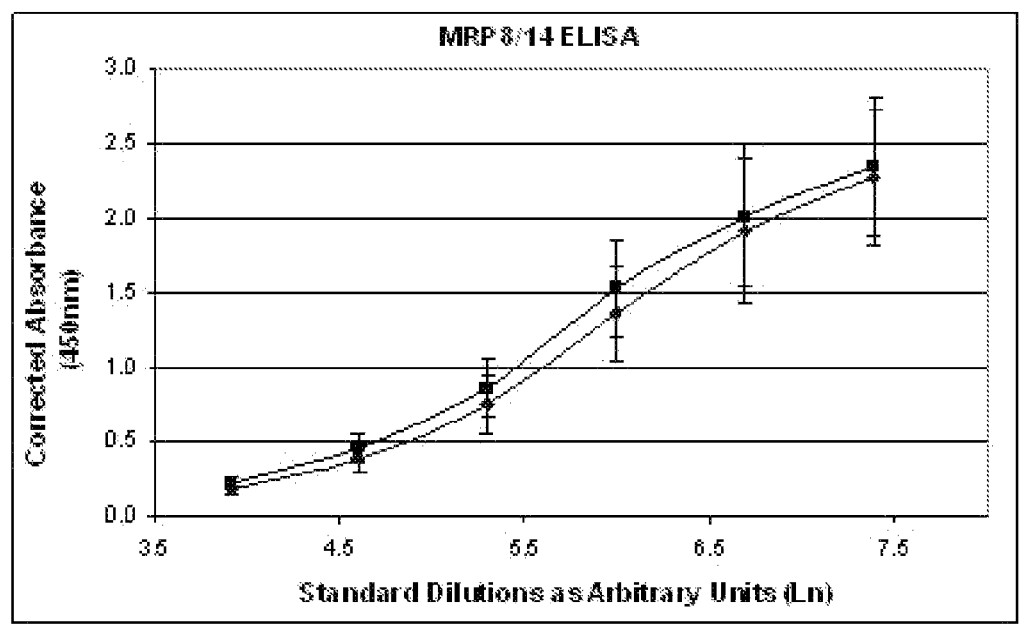
FIGURE 8

```
SEQUENCE LISTING

<160> NUMBER OF SEQ ID NOS: 8

<210> SEQ ID NO 1
<211> LENGTH: 93
<212> TYPE: PRT
<213> ORGANISM: Homo sapiens

<400> SEQUENCE: 1

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
```

```
                    50                  55                  60
Ala Val Asn Phe Gln Glu Phe Leu Ile Leu Val Ile Lys Met Gly Val
 65                  70                  75                  80

Ala Ala His Lys Lys Ser His Glu Glu Ser His Lys Glu
                 85                  90
```

<210> SEQ ID NO 2
<211> LENGTH: 114
<212> TYPE: PRT
<213> ORGANISM: Homo sapiens

<400> SEQUENCE: 2

```
Met Thr Cys Lys Met Ser Gln Leu Glu Arg Asn Ile Glu Thr Ile Ile
 1               5                  10                  15

Asn Thr Phe His Gln Tyr Ser Val Lys Leu Gly His Pro Asp Thr Leu
                20                  25                  30

Asn Gln Gly Glu Phe Lys Glu Leu Val Arg Lys Asp Leu Gln Asn Phe
             35                  40                  45

Leu Lys Lys Glu Asn Lys Asn Glu Lys Val Ile Glu His Ile Met Glu
 50                  55                  60

Asp Leu Asp Thr Asn Ala Asp Lys Gln Leu Ser Phe Glu Glu Phe Ile
 65                  70                  75                  80

Met Leu Met Ala Arg Leu Thr Trp Ala Ser His Glu Lys Met His Glu
                 85                  90                  95

Gly Asp Glu Gly Pro Gly His His Lys Pro Gly Leu Gly Glu Gly
                100                 105                 110

Thr Pro
```

<210> SEQ ID NO 3
<211> LENGTH: 15
<212> TYPE: PRT
<213> ORGANISM: Homo sapiens

<400> SEQUENCE: 3

```
Asn Ile Glu Thr Ile Ile Asn Thr Phe His Gln Tyr Ser Val Lys
 1               5                  10                  15
```

<210> SEQ ID NO 4
<211> LENGTH: 17
<212> TYPE: PRT
<213> ORGANISM: Homo sapiens

<400> SEQUENCE: 4

```
Leu Gly His Pro Asp Thr Leu Asn Gln Gly Glu Phe Lys Glu Leu Val
 1               5                  10                  15

Arg
```

<210> SEQ ID NO 5
<211> LENGTH: 114
<212> TYPE: PRT
<213> ORGANISM: Homo sapiens

<400> SEQUENCE: 5

```
Met Thr Cys Lys Met Ser Gln Leu Glu Arg Asn Ile Glu Thr Ile Ile
 1               5                  10                  15

Asn Thr Phe His Gln Tyr Ser Val Lys Leu Gly His Pro Asp Thr Leu
                20                  25                  30

Asn Gln Gly Glu Phe Lys Glu Leu Val Arg Lys Asp Leu Gln Asn Phe
             35                  40                  45
```

```
Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His Lys Pro Gly Leu Gly Glu Gly
                100                 105                 110

Thr Pro

<210> SEQ ID NO 6
<211> LENGTH: 18
<212> TYPE: PRT
<213> ORGANISM: Homo sapiens

<400> SEQUENCE: 6

Thr Glu Gly Asp Gly Val Tyr Thr Leu Asn Asn Glu Lys Gln Trp Ile
1               5                   10                  15

Asn Lys

<210> SEQ ID NO 7
<211> LENGTH: 31
<212> TYPE: PRT
<213> ORGANISM: Homo sapiens

<400> SEQUENCE: 7

Ala Val Gly Asp Lys Leu Pro Glu Cys Glu Ala Asp Asp Gly Cys Pro
1               5                   10                  15

Lys Pro Pro Glu Ile Ala His Gly Tyr Val Glu His Ser Val Arg
                20                  25                  30

<210> SEQ ID NO 8
<211> LENGTH: 406
<212> TYPE: PRT
<213> ORGANISM: Homo sapiens

<400> SEQUENCE: 8

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
                20                  25                  30

Cys Pro Lys Pro Pro Glu Ile Ala His Gly Tyr Val Glu His Ser Val
                35                  40                  45

Arg Tyr Gln Cys Lys Asn Tyr Tyr Lys Leu Arg Thr Glu Gly Asp Gly
        50                  55                  60

Val Tyr Thr Leu Asn Asp Lys Lys Gln Trp Ile Asn Lys Ala Val Gly
65                  70                  75                  80

Asp Lys Leu Pro Glu Cys Glu Ala Asp Asp Gly Cys Pro Lys Pro Pro
                85                  90                  95

Glu Ile Ala His Gly Tyr Val Glu His Ser Val Arg Tyr Gln Cys Lys
                100                 105                 110

Asn Tyr Tyr Lys Leu Arg Thr Glu Gly Asp Gly Val Tyr Thr Leu Asn
                115                 120                 125

Asn Glu Lys Gln Trp Ile Asn Lys Ala Val Gly Asp Lys Leu Pro Glu
                130                 135                 140

Cys Glu Ala Val Cys Gly Lys Pro Lys Asn Pro Ala Asn Pro Val Gln
145                 150                 155                 160
```

```
Arg Ile Leu Gly Gly His Leu Asp Ala Lys Gly Ser Phe Pro Trp Gln
                165                 170                 175
Ala Lys Met Val Ser His His Asn Leu Thr Thr Gly Ala Thr Leu Ile
            180                 185                 190
Asn Glu Gln Trp Leu Leu Thr Thr Ala Lys Asn Leu Phe Leu Asn His
        195                 200                 205
Ser Glu Asn Ala Thr Ala Lys Asp Ile Ala Pro Thr Leu Thr Leu Tyr
    210                 215                 220
Val Gly Lys Lys Gln Leu Val Glu Ile Glu Lys Val Val Leu His Pro
225                 230                 235                 240
Asn Tyr Ser Gln Val Asp Ile Gly Leu Ile Lys Leu Lys Gln Lys Val
            245                 250                 255
Ser Val Asn Glu Arg Val Met Pro Ile Cys Leu Pro Ser Lys Asp Tyr
            260                 265                 270
Ala Glu Val Gly Arg Val Gly Tyr Val Ser Gly Trp Gly Arg Asn Ala
            275                 280                 285
Asn Phe Lys Phe Thr Asp His Leu Lys Tyr Val Met Leu Pro Val Ala
290                 295                 300
Asp Gln Asp Gln Cys Ile Arg His Tyr Glu Gly Ser Thr Val Pro Glu
305                 310                 315                 320
Lys Lys Thr Pro Lys Ser Pro Val Gly Val Gln Pro Ile Leu Asn Glu
            325                 330                 335
His Thr Phe Cys Ala Gly Met Ser Lys Tyr Gln Glu Asp Thr Cys Tyr
            340                 345                 350
Gly Asp Ala Gly Ser Ala Phe Ala Val His Asp Leu Glu Glu Asp Thr
        355                 360                 365
Trp Tyr Ala Thr Gly Ile Leu Ser Phe Asp Lys Ser Cys Ala Val Ala
    370                 375                 380
Glu Tyr Gly Val Tyr Val Lys Val Thr Ser Ile Gln Asp Trp Val Gln
385                 390                 395                 400
Lys Thr Ile Ala Glu Asn
                405
```

METHODS AND DEVICES FOR DIAGNOSIS OF APPENDICITIS

CROSS-REFERENCE TO RELATED APPLICATIONS

This application is a continuation-in-part application of U.S. application Ser. No. 11/189,120 filed Jul. 25, 2005, which claims priority to U.S. provisional application Ser. No. 60/590,631 filed Jul. 23, 2004, both of which are incorporated by reference to the extent not inconsistent herewith.

BACKGROUND OF THE INVENTION

Appendicitis is a common acute surgical problem affecting human beings of a wide age range. There are approximately 700,000 cases annually in the United States. A large proportion of cases occur in the 10 to 30 age group. An accurate diagnosis at a sufficiently early stage is a significant factor in achieving a successful outcome.

Many people present to their physician with symptoms suggestive of appendicitis but caused by other ailments such as viral infections. Differentiating the appendicitis patients from those affected with other ailments is a daunting clinical task that physicians face daily. While medical science has an excellent understanding of appendicitis and its treatment, it is very limited in its ability to accurately recognize or diagnose the disease.

Complicating the goal of an accurate and early diagnosis is the considerable overlap of genuine appendicitis with other clinical conditions. There appears to be no individual sign, symptom, test, or procedure capable of providing a reliable indication of appendicitis. Imaging technology is inadequate in identifying and characterizing the appendix, especially in the early stages of the disease when treatment is likely to be most effective. Imaging technology is further handicapped by its expense and its dependence upon the availability of highly trained and experienced people to interpret the studies. This limitation affects thousands of people every year by inaccurately diagnosing their problem or by delaying the accurate diagnosis. In cases of appendicitis, delays in diagnosis are the single most important factor leading to worsening of the condition and more complications related to the disease. The misdiagnosis of appendicitis can lead not only to unnecessary surgery but also to delay of proper therapy for the actual underlying condition.

A dilemma for surgeons is how to minimize the negative appendectomy rate without increasing the incidence of perforation among patients referred for suspected appendicitis. What is desperately needed to more effectively treat this very common ailment is a simple, reliable diagnostic test that is capable of recognizing the earliest stages of the disease process.

The typical pathogenesis in appendicitis begins with obstruction of the lumen, although an initial inflammation of the organ can precede and even contribute to the obstruction. The secreted mucus of the appendix fills the closed lumen, causing an increase in intralumenal pressure and distension. The increased intralumenal pressure can exceed the level of capillary perfusion pressure, resulting in perturbation of normal lymphatic and circulatory drainage. Ultimately the appendix can become ischemic. The appendix mucosa is compromised, which can allow invasion of intralumenal bacteria. In advanced cases, perforation of the appendix may also occur with spillage of pus into the peritoneal cavity.

Currently, the diagnosis of appendicitis is difficult, and the difficulty persists during various stages in the progression of the condition. The following represents a hypothetical portrayal of stages and associated clinical presentations. Artisans of ordinary skill will recognize that a considerable degree of variation will occur in a given patient population.

At the earliest stages of inflammation, a patient can present with a variety of non-specific signs and symptoms. Upon obstruction, presentation can involve periumbilical pain, mild cramping, and loss of appetite. The progress toward increased lumenal pressure and distension can be associated with presentation involving the localization of pain to the right lower quadrant of the abdomen, nausea, vomiting, diarrhea, and low grade fever. If perforation occurs, a patient can present with severe pain and high fever. At this very advanced stage, sepsis can be a serious risk with a potentially fatal outcome.

Practitioners currently use several tools to aid in appendicitis diagnosis. These tools include physical examination, laboratory tests, and other procedures. Routine laboratory tests include complete blood count (CBC) with or without differential and urinalysis (UA). Other tests include a computed tomography (CT) scan of the abdomen and abdominal ultrasonography. Procedures can include, for example, laparoscopic examination and exploratory surgery.

Flum et al. attempted to determine whether the frequency of misdiagnosis preceding appendectomy has decreased with increased availability of certain techniques (Flum D R et al., 2001). These techniques included computed tomography (CT), ultrasonography, and laparoscopy, which have been suggested for patients presenting with equivocal signs of appendicitis. Flum et al. concluded as follows: "Contrary to expectation, the frequency of misdiagnosis leading to unnecessary appendectomy has not changed with the introduction of computed tomography, ultrasonography, and laparoscopy, nor has the frequency of perforation decreased. These data suggest that on a population level, diagnosis of appendicitis has not improved with the availability of advanced diagnostic testing." The rate of misdiagnosis of appendicitis is about 9 percent in men and about 23.2 percent in women (Neary, W., 2001).

Myeloid-related Protein Complex 8/14 (MRP8/14) is a heterodimeric complex associated with acute inflammatory conditions (for review see Striz and Trebichavsky, 2004). The complex belongs to the S100 superfamily of proteins and is also referred to S100A8/9, L1, macrophage inhibitory related protein and calprotectin. The heterodimer consists of an 8 kilodalton (MRP8) and 14 kilodalton (MRP14) subunit. MRP8 and MRP14 are alternatively named S100A8/calgranulin and S100A9/calgranulin b, respectively. MRP8/14 is a calcium binding protein originally discovered in macrophages. Neutrophils expressing high concentrations of MRP8/14 are found in a variety of inflammatory conditions, including rheumatoid arthritis, inflammatory bowel disease and allograft rejections (Frosch et al., 2000; Limburg et al., 2000; Burkhardt et al., 2001).

MRP8/14 is not always diagnostic of inflammation. For example, it does not reliably indicate the presence of inflammatory diverticuli (Gasché, C. 2005). Lymphocytes do not generally contain MRP8/14 (Hycult Biotechnology, Monoclonal Antibody to Human S100A8/A9), and therefore MRP8/14 is not diagnostic of inflammation characterized by the presence of lymphocytes but not neutrophils. Also, this protein is not always associated with opportunistic infections (Froland, M. F., et al., 1994).

Haptoglobin is an acute phase protein that binds free hemoglobin following hemolysis. The haptoglobin-hemoglobin complex is removed by the liver. Haptoglobin is a heterotetramer composed of two alpha and two beta subunits. The alpha and beta units are derived from a single polypeptide chain precursor that is enzymatically cleaved to produce the subunits. The molecular weights of the subunits are approximately 9 kd-18 kd and 38 kd for alpha and beta, respectively.

In addition to being a hemoglobin scavenger, haptoglobin has a wide range of biological functions (Dobryszycka, 1997). Haptoglobin has been shown to be upregulated and modulate the immune response in certain infection and inflammatory conditions perhaps by regulating monocyte function (Arredouani et al., 2005). The alpha subunit has been demonstrated to be a potentially useful serum marker for ovarian cancer (Ye et al., 2003).

Without a reliable method for inexpensively testing the presence and severity of acute appendicitis, physicians must rely on costly imaging tests such as CT scans to tell them whether or not the patient truly has acute appendicitis and the urgency of appendectomy. Furthermore, these imaging tests usually involve delays of several hours that could be used for appropriately treating the patient. A method is needed to reduce the number of such costly scans. If a substantial fraction of CT scans could be avoided, savings of $3,000-$5,000 per scan could be saved for each patient. Healthcare costs for Individuals, hospitals, health insurance providers and the healthcare system as a whole could be substantially reduced. In addition, such a reliable method will allow physicians to more appropriately and efficiently diagnose and management the treatment of appendicitis patients.

SUMMARY OF THE INVENTION

This invention provides a method for scoring the severity of appendicitis of a patient suspected of suffering from appendicitis comprising testing a sample from the patient for the quantity of MRP8/14 in said sample and comparing the quantity of MRP8/14 in the sample with the quantity of MRP8/14 in one or more standard samples, containing quantities of MRP8/14 previously correlated with one or more grade scores for appendicitis severity; and assigning to the severity of appendicitis in the patient the grade score of the standard sample that has the quantity of MRP8/14 closest to the quantity of MRP8/14 present in the patient sample.

Scoring the severity of appendicitis means providing a series of words or numbers or other indicators ranked in order of the severity of the appendicitis, for example as defined by the stages and clinical presentations described above in the Background section, or as defined histologically as described below. The AppyScore™ grading system of an embodiment of this invention is based on histologically-determined appendicitis severity grades.

A patient suspected of suffering from appendicitis, presents with at least some classical symptoms of appendicitis. Such classical symptoms of appendicitis include pain in the abdomen; pain that starts near the navel, then moves to the lower right quadrant of the abdomen; anorexia (loss of appetite); trouble eating accompanied by sleepiness; nausea starting after onset of pain; vomiting starting after onset of pain; vomiting accompanied by fatigue; constipation; small stools with mucus; diarrhea; inability to pass gas; low-grade fever; abdominal swelling; pain in the abdomen worsening; tenesmus (feeling of needing to move the bowels); high fever; and leukocytosis. Increased plasma viscosity is also associated with appendicitis. In one embodiment of the invention at least two or more symptoms of appendicitis are identified.

The patient is tested to quantify the amount of MRP8/14 in a sample from the patient. MRP8/14 is a molecule that the inventors have found to be differentially associated with appendicitis.

In one embodiment of this invention patients are screened to determine whether or not they have an "interfering condition," i.e., another condition in which the molecule is present in the type of sample being tested. Patients can be tested for the presence of the molecule if they do not have such an interfering condition. Interfering conditions include recent allograft; septicemia; meningitis; pneumonia; tuberculosis; rheumatoid arthritis; gastrointestinal cancer; inflammatory bowel disease; skin cancer; periodontitis, preeclampsia, and AIDS.

A sample can be a fluid or tissue, and can contain whole blood, plasma, serum, milk, urine, saliva and/or cells. Fecal samples may also be used. Preferably tissue and fecal samples are liquefied before testing. However, previously-known tests using fecal samples produce too many false negative results, and blood, plasma and serum provide more accurate results. In embodiments of this invention the patient sample is a blood sample, and as will be appreciated by those of skill in the art, the term "sample from a patient" or "patient sample" as used herein includes plasma, serum and other products derived from blood in which MRP8/14 can be found, including dilutions of the foregoing components.

The inventors hereof have discovered that the quantity of MRP8/14 in patient blood samples is correlated with the severity of appendicitis. Quantification of the amount of MRP8/14 can be done in terms of absolute quantities, e.g., micrograms per milliliter, or in terms of standards based on analysis of MRP8/14 in samples taken from patients having appendicitis of known severity, for example, using measurement parameters other than absolute quantities, such as absorbance readings from a microplate reader.

The quantity of MRP8/14 in the patient sample is compared with that present in standard samples taken from patient(s) with previously-known appendicitis severity grade scores, and the severity of the patient's appendicitis is assigned the score previously assigned to whatever standard sample has a quantity of MRP8/14 closest to that of the patient sample.

In an embodiment of this invention, using a system of grading the severity of appendicitis developed by the inventors hereof, the grade scores for appendicitis severity correspond to histological condition of patient tissue. These grade scores are referred to herein as AppyScore™ grades, and are defined as follows:

| | |
|---|---|
| Grade 1 | No identifiable inflammation in appendix tissue; |
| Grade 2 | Inflammation extending through the mucosa and into the submucosa of the appendix; |
| Grade 3 | Inflammation extends past the submucosa into the muscular levels of the appendix; |
| Grade 4 | All layers of the appendix, including the serosa, inflamed, and perforation identified. |

Standard samples correlated to each of these grades are used in an embodiment of this invention.

As will be appreciated by those skilled in the art, the standard data may be expressed in terms of absolute quantities, e.g., micrograms per milliliter, or in terms of assigned units mathematically related to absolute quantities of MRP8/14 correlated with appendicitis severity grade scores, e.g., the AppyScore™ units described herein that are correlated to the four histologically-based grades described above.

The standards of the present invention are based on dilutions optimized to provide MRP8/14 concentrations in the ranges useful for scoring appendicitis severity.

The standard data is based on average AppyScore™ grades for patients known to have histologically-based grade scores as described above. As shown in FIG. 11, these AppyScore™ grades have been shown to have an excellent linear relationship to the histologically-based grade scores, which gives the AppyScore™ methods of this invention strong predictive power. As will be appreciated by those skilled in the art, statistically, in isolated instances, a given patient's AppyScore™ value may not accurately reflect that patient's histology. Nevertheless, the AppyScore™ values provide physicians with an important tool for assessing appendicitis severity without the need to refer to any accompanying histology.

In one embodiment of this invention two or more molecules differentially associated with appendicitis are tested for. Identification of additional molecules provides greater accuracy to the method.

One molecule differentially associated with appendicitis is MRP8/14. Another is haptoglobin. Both these molecules can be tested for in diagnosing appendicitis. MRP8/14 levels in the range of about 1 to about 11 pg/ml are present in patients without appendicitis. Levels higher than this provide increased accuracy in diagnosing appendicitis. Levels higher than about 10, 11, 13, 15 or 20 μg/ml of MRP8/14 can be used to diagnose appendicitis. Haptoglobin levels in the range of about 27-139 mg/dL are found in patients without appendicitis. Levels higher than this, e.g., higher than 125, 130, 135, 139 and 150 provide increased accuracy in diagnosing appendicitis. Levels of 200 μg/ml indicate severe appendicitis.

Other molecules that can be tested for in the methods of this invention, or that can be tested for in addition to the foregoing molecules, include unique structural proteins of the gastrointestinal tract, stress-related inflammatory mediators, immunologic factors, indicators of intestinal bacterial flora, Plasminogen Activator Inhibitor-1, fatty acid binding proteins, nuclear factor kappa beta (NFκB), specific appendix antigens (HLA-DR), inflammation associated antigens; and nucleic acids coding for any of the foregoing, including nucleic acids coding for MRP8/14 and haptoglobin. Methods for testing for the presence of nucleic acids are known to the art.

Determining the quantity and presence of MRP8/14 in the sample from a patient is done by a method including determining the amount of binding of MRP8/14 in said sample to an antibody or antibodies specific to MRP8/14. Antibodies specific to MRP8/14 include monoclonal and polyclonal antibodies raised to this antigen. The term "antibodies to MRP8/14" also includes antibody fragments capable of binding to MRP8/14 as known to the art. Other antibodies capable of binding to MRP8/14 can be used in the methods as well, such as antibodies raised to the subunits of the MRP8/14 complex, namely MRP8 and MRP14. Such antibodies can be used as detection antibodies to bind to an immunocomplex between MRP8/14 and an antibody specific thereto in an ELISA-type immunoassay. Monoclonal and polyclonal antibodies that bind to MRP8/14 can be prepared by methods known to the art. Antibodies for MRP8/14, MRP8 and MRP14 are commercially available through Cell Sciences, Canton, Mass. In one embodiment of this invention, the antibody specific to MRP8/14 is the monoclonal antibody 27e10 supplied by Cell Sciences, Inc., which binds to the junction between MRP8 and MRP14 in the MRP8/14 dimer.

Monoclonal antibodies to haptoglobin useful in the methods of this invention are also known to the art, e.g., as described in U.S. Pat. No. 5,552,295.

The methods for diagnosing appendicitis can include using test devices, e.g., cartridge test devices and dipstick test devices, and/or other means for determining the presence or absence of MRP8/14, e.g., performing western blots, northern blots, ELISA tests, protein function tests, PCR and other assays known to the art. Cartridge immunoassays can be designed to provide information on relative amounts of such molecules as described herein. Other assays known to the art including ELISAs and hospital assay devices such as the Synchron LX system of Beckman Coulter can be used to provide the amount of MRP8/14 present in the patient sample, which can then be compared with amounts present in patients without appendicitis to determine whether or not the patient has appendicitis.

Test devices can be in the form of cartridges, dipsticks, or other conformations known to the art. The test device can also be part of a kit which can contain instructions for use, instructions for comparison of test results with results of the same test done on non-appendicitis patient, additional reagents, such as cells or fluids from non-appendicitis patients, and other reagents known to the art. These types of assay devices are known to the art and described, e.g., in U.S. Patent Publication No. 2003/0224452.

When the sample is blood, the method can also include processing the blood by a means known to the art, such as filtration or centrifugation, for separating plasma or serum which is to be assayed.

The immunoassays and procedures of this invention can be used in methods for medical management of patients suspected of having appendicitis. "Medical management" means determining the severity of the appendicitis condition and deciding what treatment plan to use for the patient. For example, formulating a treatment plan requires decisions regarding anticipated length of hospital stay; antibiotics dosage; type of antibiotics; timing of administration of antibiotics; and timing of surgery.

As a first step in the method for medical management, a patient sample can be tested by contacting the sample with an immunoassay device such as that described in U.S. patent application Ser. No. 11/189,120, for determining the degree of binding of MRP8/14 in the sample to an anti-MRP8/14 antibody wherein a visually-detectable signal is produced in the immunoassay device in response to a degree of binding that indicates whether or not the patient has appendicitis.

If use of this immunoassay device provides a signal that indicates the presence of appendicitis, a second immunoassay can be performed on a patient sample comprising comparing the degree of binding of MRP8/14 in the sample to an antibody or antibodies to MRP8/14 to the degree of binding to anti-MRP8/14 antibody or antibodies of MRP8/14 in a standard sample containing an amount of MRP8/14 correlated to a predetermined appendicitis grading category.

Alternatively, the first step can be skipped, and the second immunoassay can be performed and used both for diagnosis of whether or not the patient has appendicitis and for evaluating the severity of the appendicitis.

In one embodiment of the invention, the grading categories described above that are based on histological evaluations, can be used to score the severity of the appendicitis.

The second immunoassay can be any immunoassay known to the art that is capable of quantitatively evaluating MRP8/14 in the sample. In one embodiment it is an ELISA.

If the immunoassay(s) indicate that the patient does not have appendicitis, the patient can be examined for other conditions having symptoms consistent with those of the patient.

This invention also provides an immunoassay kit for determining the severity grade of appendicitis comprising an anti-MRP8/14 antibody and a means for detecting an immunoreaction product comprising MRP8/14 and the antibody. The immunoassay kit can also comprise a specific binding agent capable of binding to said anti-MRP8/14 antibody or to MRP8/14, at least one enzyme-linked immunosorbent assay surface, a standard curve or data set showing a correlation of the quantity of MRP8/14 with appendicitis severity and/or at least one MRP8/14 standard.

The invention also comprises a standard samples or a set of standard samples each comprising a quantity of MRP8/14 known to be present in samples from patients having a known appendicitis grade, wherein each standard sample in the set comprises a different quantity of MRP8/14.

This invention also provides a standard curve or data set including a data set in an electronic storage medium comprising data representative of MRP8/14 quantities correlated with appendicitis grades for which said quantities are diagnostic. The electronic storage medium can be in a computer processor, or a CD, disc, tape, DVD or other storage medium known to the art.

This invention further provides a method of scoring the severity of appendicitis corresponding to histological condition of tissue of a patient suspected of suffering from appendicitis. The method comprises examining tissue of the appendix and optionally tissue adjacent thereto from the patient and assigning grade scores to describe the severity of appendicitis in the patient corresponding to the following condition of the tissue as follows: Grade 1: No identifiable inflammation in appendix tissue; Grade 2: Inflammation extending through the mucosa and into the submucosa of the appendix; Grade 3: Inflammation extends past the submucosa into the muscular levels of the appendix; Grade 4: All layers of the appendix, including the serosa, inflamed, and perforation identified.

BRIEF DESCRIPTION OF THE FIGURES

FIG. 7: Haptoglobin distribution. Haptoglobin western blot analysis of normal (N) and diseased (A) tissue. The numbers are sample ID numbers. Molecular weights are shown in kilodaltons. The alpha and beta subunits are 9-16 kd and 38 kd, respectively.

FIG. 8: Comparison of biological plasma reference standards: new reference standard (■) and current reference standard (♦). Each value represents the mean of triplicate determinations obtained from three ELISA plates±standard deviation.

DETAILED DESCRIPTION

Figure 1A:
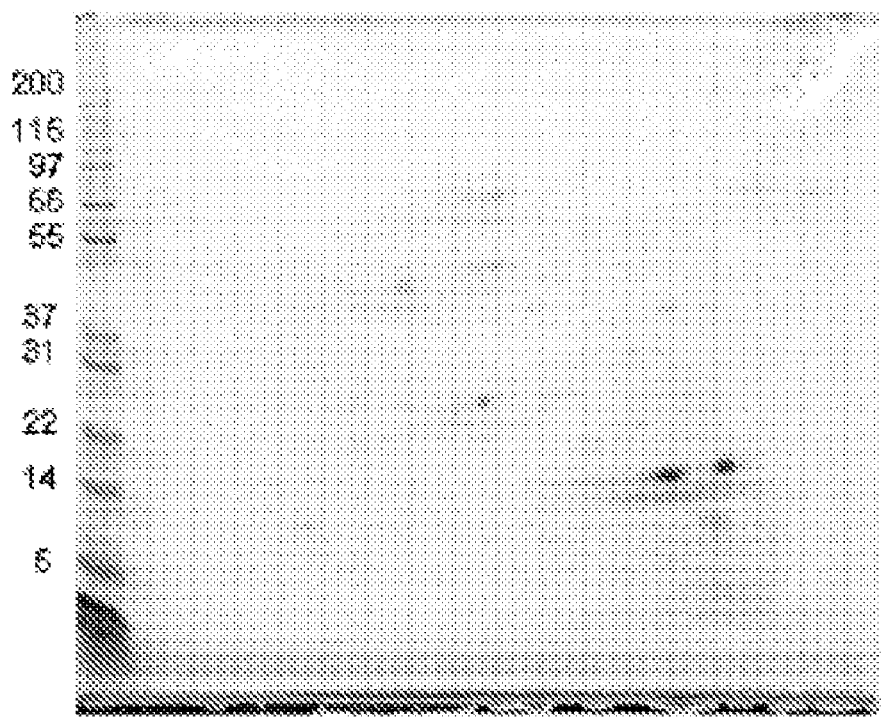
FIG. 1: Two-dimensional electrophoresis image of proteins from (A) normal and (B) diseased appendix tissue. Proteins were separated by isoelectric focusing on the x axis and by molecular weight on the y axis. The molecular weight in kilodaltons is shown on the left. The arrow indicates the upregulated protein, AP-93.

The vermiform appendix is recognized as a separate organ from the large and small intestines. It extends as a finger-like pouch from the base of the ascending colon, which is also called the cecum. The appendix, like the large intestine, is hollow and composed of the same three tissue layers. These three layers are a mucosa, muscularis and a serosa. The appendiceal lumen communicates with the lumen of the cecum via a round opening (os) through which the appendix adds its secretions to the fecal stream. These secretions are excess mucus produced from the appendiceal mucosa. In addition to containing mucus, the appendix also contains numerous bacteria common to the right colon. Obstruction of the appendiceal lumen is the dominant factor causing acute appendicitis. While fecaliths are the usual cause of appendiceal obstruction, hypertrophied lymphoid tissue, inspissated barium from previous x-ray studies, vegetable and fruit seeds, and intestinal worms like ascarids can also block the appendiceal lumen.

Following luminal obstruction an escalating cycle of events ensues. The proximal obstruction of the appendix produces a closed-loop obstruction that blocks the normal flow of appendiceal mucus into the cecum. The continuing normal secretion of the appendiceal mucus very rapidly fills the luminal capacity of the appendix (approximately 0.1 cc). Once the luminal capacity of the appendix is reached additional mucus production from the obstructed appendix rapidly elevates the intraluminal pressure within the organ. This elevated intraluminal pressure is exerted outward against the appendiceal wall and causes the appendix to distend. Distention stimulates nerve endings of the visceral afferent pain fibers, producing vague, dull, diffuse pain in the midabdomen or lower epigastrium. Peristalsis is also stimulated by the rather sudden distention, so that some cramping may be superimposed on the visceral pain early in the course of appendicitis.

Distention of the appendix continues, not only from continued mucosal secretion, but also from rapid multiplication of the resident bacteria of the appendix. As pressure in the organ increases, venous pressure within the appendiceal wall is exceeded. This rising intraluminal pressure then occludes capillaries and venules, but arteriolar inflow continues, resulting in engorgement and vascular congestion. Distention of this magnitude usually causes reflex nausea and vomiting, and the diffuse visceral pain becomes more severe. The inflammatory process soon involves the serosa of the appendix and in turn parietal peritoneum in the region, producing the characteristic shift in pain to the right lower quadrant (RLQ). The disease process is fairly advanced when pain is localized to the RLQ.

The mucosa of the gastrointestinal tract, including the appendix, is very susceptible to impaired blood supply. Thus mucosal integrity is compromised early in the process, allowing bacterial invasion of the deeper tissue layers. This bacterial invasion leads to appendiceal destruction and systemic liberation of various bacterial toxins. Fever, tachycardia, and leukocytosis develop as a consequence of this systemic release of dead tissue products and bacterial toxins. As progressive appendiceal distention rises, encroaching on the arteriolar pressure, ellipsoidal infarcts develop in the antimesenteric border of the appendiceal serosa. As distention, bacterial invasion, compromise of vascular supply and infarction progress, perforation occurs through one of the infarcted areas on the antimesenteric border. This perforation then releases the bacteria and its toxins into the abdominal cavity.

Appendicitis has been called the "great imitator," as its symptoms are frequently confused with those of other conditions. This confusion stems from the nonspecific nature of the pain early in its course and the variability in how appendicitis progresses. There are many medical conditions having symptoms that are confused with those of appendicitis. These include conditions of the gastrointestinal tract including viral or bacterial gastroenteritis, inflammatory bowel disease, intestinal obstruction, intussusception, bacterial or viral mesenteric adenitis, Meckel's diverticulitis, peptic ulcer, severe constipation and typhlitis; gynecologic conditions such as mittelschmerz, pelvic inflammatory disease, ruptured ovarian cyst, ruptured tubal pregnancy, torsion of normal ovary or ovarian cyst or tumor; hepatobiliary/pancreatic conditions such as cholecystitis/cholelithiasis and pancreatitis; traumas including rectus hematoma, solid/hollow organ injury, and trauma to a previously-unsuspected mass (Wilm's tumor, lymphoma, etc.; conditions of the urinary tract such as cystitis, hydronephrosis, pyelonephritis, and renal stone; as well as other conditions including diabetic ketoacidosis, helminthic infestation, hemolytic uremic syndrome, hemophilia A, Henoch-Schonlein purpura, lupus erythematosus, porphyria, primary peritonitis, right-sided pneumonia, sickle-cell crisis, streptococcal infection, torsion of appendix epiploica, and torsion of omentum.

Pain in the right lower quadrant of the abdomen is the hallmark of appendicitis but this is not typically what the patient first perceives. When the appendiceal lumen first obstructs, the patient will have few if any symptoms because the appendiceal lumen has not yet had the chance to fill with mucus. The time required to fill the appendiceal lumen is proportional to the lumen volume available behind the obstruction. This is variable and unpredictable, as that volume is dependent upon the individual's appendix size and precisely where the fecalith or other obstruction is located along that length. Should the fecalith or other obstruction be close to the tip of the appendix the available volume is relatively small and the time to symptoms or perforation short. In contrast, the opposite will be true should the fecalith or other obstruction be near the base of the appendix and provide for the largest possible appendiceal volume.

Once the appendix begins to distend, the appendicitis patient will begin to experience a nonspecific discomfort usually in the mid portion of the abdomen. This discomfort can be easily confused with common ailments such as indigestion, constipation or a viral illness. Continued appendiceal distention is also accompanied by some nausea and frequently vomiting. Rarely is the vomiting severe or unrelenting, which reinforces the confusion with common ailments.

Later in the progression of appendicitis, inflammation will have progressed to the outermost layer of the appendix. This outmost layer is called the serosa and it touches the inner lining of the abdominal cavity called the peritoneum. This contact irritates the peritoneum, producing peritonitis that is perceived by the appendicitis patient as focal pain wherever the appendix is touching the peritoneum. This too can vary between different individuals. The appendix is most usually located in the right lower quadrant under an area known as McBurney's point. McBurney's point is a position on the abdomen that is approximately two-thirds of the distance from the anterior superior iliac spine in a straight line toward the umbilicus. The appendix can, however, reside in other locations in which case the peritonitis produced by the appendix will be in an atypical location. This again is a common factor producing an erroneous diagnosis and delays surgical treatment in cases of appendicitis.

Regardless of its location, if appendicitis is allowed to progress the organ will eventually perforate. This contaminates the abdominal cavity around the perforated appendix with bacteria producing a severe infection. This infection will usually lead to a localized intra-abdominal abscess or phlegmon and can produce generalized sepsis.

To identify molecules differentially associated with appendicitis, a proteomic approach was used. A protein complex, MRP8/14, that is present in appendix tissue in patients with acute appendicitis was identified. The highly correlative nature of this complex with appendicitis led us to examine MRP8/14 serum and plasma levels in patients with apparent appendicitis. MRP8/14 is significantly elevated ($p<0.02$) in patients with appendicitis as compared to levels in patients with apparent appendicitis yet having no appendiceal inflammation. The source of MRP8/14 in the serum is the inflamed appendix tissue. This is consistent with the known functions of MRP8/14.

Without being bound by any theory as to the mechanism of action of the present invention, the following discussion is provided in an attempt to explain the presence of MRP8/14 in increasing amounts correlated with appendicitis severity. The role of MRP8/14 in inflammation is not fully understood but it does seem to play a vital role in retaining leukocytes in microcapillaries. Extracellular MRP8/14 interacts with endothelial cells by binding to heparin sulfate and specifically carboxylated glycans (Robinson et al., 2002). The intracellular signal pathways and effector mechanisms induced by binding of MRP8/14 to endothelial cells are not well defined. However, interaction of MRP8/14 with phagocytes increases binding activity of the integrin receptor CD11b-CD18. This is one of the major adhesion pathways of leukocytes to vascular endothelium (Ryckman et al., 2003). It is believed that the MRP8/14 utilizes the receptor for advanced glycation end products (RAGE) (Hsieh et al., 2004). Neutrophils are white blood cells that are the first to migrate from the circulation into sites of inflammation. Within neutrophils, constituting approximately 40% of total cytosolic proteins is the MRP8/14 complex. This protein is specifically expressed only in cells of macrophage lineage, making blood monocytes and acutely activated macrophages other potential white blood cell sources of these proteins. MRP8/14 is not usually expressed in lymphocytes nor resident macrophages or those macrophages involved in chronic inflammation. These two proteins are also known to be independently expressed by mucosal epithelium in specific states of acute inflammation.

In the case of appendicitis, the luminal obstruction and the resultant distention of the appendiceal wall triggers an inflammatory response. The circulating neutrophils are then recruited into the area, as are activated macrophages. While the expression of this protein complex is related to the activity of the macrophages in inflammation, the exact relationship between MRP8/14 and cellular activity is not fully known. What is known is that the intracellular distribution of MRP8/14 varies with the activation state of macrophages. Normal macrophages contain the complexes in the cytosol, but once stimulated, MRP8/14 translocates from the cytosol to the cell membrane (specifically with the proteins of the cytoskeleton). This would imply that MRP8/14 may be related to cell movement, phagocytosis or inflammatory signal transduction. The roles of cellular movement and signal transduction may also explain why MRP8/14 is produced directly from vascular epithelium such as that lining the blood vessels within the appendix.

Regardless of its role in certain inflammatory conditions, MRP8/14's abundance within cells of acute inflammation makes it an excellent detector and monitor of acute appendicitis. The first step in the inflammatory process is the recruitment of neutrophils and macrophages to a specific site. In our study, the specific site is the appendix, where those MRP8/14-containing cells will engage the offending stimulus.

This engagement will usually result in MRP8/14 cell death and the liberation of MRP8/14 from either the cytosol or cell membrane into the patient's circulation. At the same time, the mucosal linings of the appendix will start to produce and release MRP8/14 to facilitate macrophage migration or inflammatory amplification. This process will then escalate as increasing amounts of MRP8/14 cells are recruited by the appendicitis to ultimately release more MRP8/14 into the circulation. Other examples of inflammatory states causing increases of extracellular MRP8/14 and the tendency of these increases of MRP8/14 to correlate with extent of inflammation are known. Specifically, chronic bronchitis, cystic fibrosis and rheumatoid arthritis are all associated with elevated serum levels of MRP8/14 and the severity of these diseases is generally proportional to the serum levels of MRP8/14 detected.

The physiological role of MRP8/14 suggests that it could be an ideal clinical marker for acute appendicitis. As patients with appendicitis are generally young and healthy, they generally produce a vigorous inflammatory response. This vigorous response is believed to liberate MRP8/14 in the earliest stages of the disease, which then escalates as appendicitis progresses. Additionally, the diseases known to be associated with elevated levels of MRP8/14 are not common in this younger age group and usually do not produce symptomology similar to appendicitis. Finally, as MRP8/14 is not located in nor associated with lymphocyte proliferation, this marker is not believed to be elevated in viral infections. This is an especially powerful advantage for diagnosing appendicitis, as viral infections are one of the most common imitators of appendicitis.

Haptoglobin was also identified as a useful marker for appendicitis. A differential proteomic screen of depleted serum identified haptoglobin as a marker for appendicitis. A second differential screen of appendix tissue confirmed that haptoglobin is upregulated in the appendix tissue of patients with appendicitis. This finding was confirmed by western blotting of tissue protein. In particular the alpha subunit isoforms were present only in diseased tissue. Since haptoglobin is a plasma protein, it is highly valuable as a biomarker for appendicitis.

As discussed above, this invention provides a method for scoring the severity of appendicitis of a patient suspected of suffering from appendicitis comprising testing a sample from the patient for the quantity of MRP8/14 in said sample and comparing the quantity of MRP8/14 in the sample with the quantity of MRP8/14 in one or more standard samples, containing quantities of MRP8/14 previously correlated with one or more grade scores for appendicitis severity; and assigning to the severity of appendicitis in the patient the grade score of the standard sample that has the quantity of MRP8/14 closest to the quantity of MRP8/14 present in the patient sample. The AppyScore™ grading system of an embodiment of this invention is based on histologically-determined appendicitis severity grades.

The patient sample is preferably a blood sample, and as will be appreciated by those of skill in the art, the term "sample from a patient" or "patient sample" as used herein includes plasma, serum and other products derived from blood in which MRP8/14 can be found, including dilutions of the foregoing components. In one embodiment of the invention, the sample is taken from a patient thirty years old or younger.

MRP8/14 is a molecule that has been found by the present inventors to be differentially associated with appendicitis. The inventors hereof have also discovered that the quantity of MRP8/14 in patient blood samples is correlated with the severity of appendicitis. Quantification of the amount of MRP8/14 can be done in terms of absolute quantities, e.g., micrograms per milliliter, or in terms of standards based on analysis of MRP8/14 in samples taken from patients having appendicitis of known severity, for example, using measurement parameters other than absolute quantities, such as absorbance readings from a microplate reader.

The test can use separate antibodies to the MRP8 and MRP14 subunits to test for quantities of MRP8/14 in the sample. If there is a 1:1 molar ratio of the quantity of MRP8 and MRP14, then it can be assumed the MRP8 and MRP14 are present in complexed form as MRP8/14 and that no additional MRP8 or MRP14 is present in the sample. Even if there is a greater or lesser ratio than 1:1 of MRP8:MRP14, a threshold value for one of these components consistent with sufficient MRP8/14 to indicate the presence of appendicitis, can be used to diagnose appendicitis, so long as there is an equivalent molar amount of the other component in the sample.

The quantity of MRP8/14 in the patient sample is compared with that present in standard samples taken from patient(s) with previously-known appendicitis severity grade scores, and the severity of the patient's appendicitis is assigned the score previously assigned to whatever standard sample has a quantity of MRP8/14 closest to that of the patient sample. In the simplest version of the method, the patient sample is compared with only a single patient sample, for example, a standard sample having a quantity of MRP8/14 that is the least quantity that can be used to reliably distinguish patients having appendicitis from those not having appendicitis. In other versions of the method, the patient sample is compared with a plurality (two or more) standard samples, for example one standard sample for distinguishing patients having appendicitis from those not having appendicitis and a second standard sample for distinguishing patients having perforated appendices. In still other versions, additional standard samples are used to define intermediate grades of appendicitis severity.

In an embodiment of this invention, using a system of grading the severity of appendicitis developed by the inventors hereof, namely, the AppyScore™ system described above, the four grade scores for appendicitis severity correspond to histological condition of patient tissue. Standard samples correlated to each of these grades are used in a preferred embodiment of this invention.

The standard samples can be individual samples from patients having a known appendicitis severity grade, or each standard sample can be a pooled sample or aliquot thereof taken from multiple patients having appendicitis of a single known grade. Standard samples can also be prepared by adding to a suitable carrier, such as buffer, serum, plasma, blood or other suitable carrier known to the art, a predetermined amount of MRP8/14 corresponding to an amount present in patients having appendicitis of a known grade. The MRP8/14 can be obtained by any means known to the art, as by isolation from blood or blood products such as commercially available plasma, of humans or other mammals in which it is known to be present, or by expression of recombinant MRP8/14. In addition, MRP8/14 can be made from naturally-occurring isolated or recombinant MRP8 and MRP14 by the methods described in Hessian (2001).

As will be appreciated by those skilled in the art, the comparison of sample MRP8/14 with the standard may be conveniently done by comparing the MRP8/14 measurement from the patient sample with a compilation of data representing quantities of MRP8/14 present in standard samples from patients having known appendicitis grades, the quantity of MRP8/14 in each said standard sample being correlated with the appendicitis grade of the patient from which it was taken. Such data may be in the form of a standard curve or compiled in the form of a database electronically stored in a computer processor. Again, as will be appreciated by those skilled in the art, the standard data may be expressed in terms of absolute quantities, e.g., micrograms per milliliter, or in terms of assigned units mathematically related to absolute quantities of MRP8/14 correlated with appendicitis severity grade scores, e.g., the Appyscore™ units described herein that are correlated to the four histologically-based grades described above.

When the standard data is stored in a computer processor, the comparison of patient results with standards can be made by a method comprising inputting data representing the quantity of MRP8/14 in the patient sample into the computer processor and allowing the computer processor, which has been preprogrammed for the purpose, to calculate and display the patient's appendicitis severity score.

The MRP8/14 test of this invention can be included as one of a panel of blood tests analyzed by an automated blood testing system, such as the Abbott Prism™ system. In this case, the test results representing the quantity of MRP8/14 in the patient sample are generated by the automated system, which also comprises detection means for detecting binding of MRP8/14 in the sample with an antibody to MRP8/14.

Determining the quantity and presence of MRP8/14 in the sample from a patient is done by a method including determining the amount of binding of MRP8/14 in the sample to an antibody or antibodies specific to MRP8/14. Antibodies specific to MRP8/14 include monoclonal and polyclonal antibodies raised to this antigen. The term "antibodies to MRP8/14" also includes antibody fragments capable of binding to MRP8/14 as known to the art. Other antibodies capable of binding to MRP8/14 can be used in the methods as well, such as antibodies raised to the subunits of the MRP8/14 complex, namely MRP8 and MRP14. Such antibodies can be used as detection antibodies to bind to an immunocomplex between MRP8/14 and an antibody specific thereto, in an ELISA-type immunoassay. In one embodiment of this invention, the antibody specific to MRP8/14 is the monoclonal antibody 27e10 supplied by Cell Sciences, Inc., which binds to the junction between MRP8 and MRP14 in the MRP8/14 dimer and does not recognize MRP8 or MRP14 alone. This antibody is also useful in the event that some MRP8/14 in the sample is in the form of a heterotetramer (two MRP8 subunits and two MRP14 subunits).

Monoclonal and polyclonal antibodies that bind to MRP8/14 can be prepared by methods known to the art. Particular amino acid sequences that can be used for preparing such antibodies include the sequence of MRP8: MLTELEKALN-SII DVYHKYSLIKGNFHAVYRDDLKKL-LETECPQYIRKKGADVWFKELDINTDGAVNF QEF-LILVIKMGVAAHKKSHEESHKE [SEQ ID NO:1] and the sequence of MRP14: MTCKMSQLERNIETIINTFHQYS-VKLGHPDTLNQGEFKELVRKDLQNFL KEN-KNEKVIEHIMEDLDTNADKQLSFEEFIM-LMARLTWASHEKMHEGD GPGHHHKPGLGEGTP [SEQ ID NO:2]. Such antibodies can be made by methods known to the art, including those comprising injecting a suitable animal such as a mouse with neutrophils containing MRP8/14, or isolated MRP8/14, recombinant MRP8/14, or MRP8/14 synthesized from MRP8 and MRP14 by inducing heterodimer formation as discussed above.

The immunoassays and procedures of this invention can be used in methods for medical management of patients suspected of having appendicitis. "Medical management" means determining the severity of the appendicitis condition and deciding what treatment plan to use for the patient. For example, formulating a treatment plan requires decisions regarding anticipated length of hospital stay; antibiotics dosage; type of antibiotics; timing of administration of antibiotics; and timing of surgery. Knowledge of the severity of a patient's appendicitis condition at a given time can also help the physician determine whether the patient should be sent for CT scan, should simply be observed for a period of time and then retested by the methods of this invention to determine the severity of the appendicitis condition, or should be immediately sent to surgery for an appendectomy. The risk of secondary infection after appendectomy can be predicted using the methods of this invention. For example, an AppyScoreTm result of Grade 2 would generally indicate a risk of secondary infection of only about 5% or less. A Grade 3 score might raise the risk to about 10 to 15%, while a Grade 4 score would alert to the physician that the risk of secondary infection is probably 30% or more. Physicians can then decide whether narrow or broad-spectrum antibiotic agents are indicated.

In the unlikely event a patient has an AppyScore™ result of Grade 2 and extended observation and/or CT scan do not indicate acute appendicitis, it is possible the patient is suffering from chronic appendicitis, and can be treated accordingly.

As a first step in the method for medical management, a patient sample can be tested by contacting the sample with an immunoassay device such as that described in U.S. patent application Ser. No. 11/189,120, for determining the degree of binding of MRP8/14 in the sample to an anti-MRP8/14 antibody wherein a visually-detectable signal is produced in the immunoassay device in response to a degree of binding that indicates whether or not the patient has appendicitis. This immunoassay device can be a simple lateral flow or dipstick or similar device that can be used in the doctor's office or Emergency Room to quickly separate patients having appendicitis from those not having appendicitis.

If use of this immunoassay device provides a signal that indicates the presence of appendicitis, a second immunoassay can be performed on a patient sample comprising comparing the degree of binding of MRP8/14 in the sample to an antibody or antibodies to MRP8/14 to the degree of binding to anti-MRP8/14 antibody or antibodies of MRP8/14 in a standard sample containing an amount of MRP8/14 correlated to a predetermined appendicitis grading category.

Alternatively, the first step can be skipped, and the second immunoassay can be performed and used both for diagnosis of whether or not the patient has appendicitis and for evaluating the severity of the appendicitis.

In one embodiment of the invention, the grading categories described above that are based on histological evaluations, can be used to score the severity of the appendicitis.

The second immunoassay can be any immunoassay known to the art that is capable of quantitatively evaluating MRP8/14 in the sample. In one embodiment it is an ELISA. Samples and standards may require dilution prior to performing the immunoassay. In one embodiment, patient samples are diluted at least about 100-fold for use in the ELISA test. An ELISA immunoassay may also comprise means as known to the art for testing standard and/or control samples. The ELISA can also comprise means for testing standard and control samples. This immunoassay should be capable of completion in as short a time as possible. In an embodiment an ELISA immunoassay of this invention can be completed within sixty minutes or less.

If the immunoassay(s) indicate that the patient does not have appendicitis, the patient can be examined for other conditions having symptoms consistent with those of the patient as described above.

Immunoassay kits of this invention for determining the severity grade of appendicitis can comprise an anti-MRP8/14 antibody and a means for detecting an immunoreaction product comprising MRP8/14 and the antibody. The immunoassay kit can also comprise a specific binding agent capable of binding to said anti-MRP8/14 antibody or to MRP8/14, at least one enzyme-linked immunosorbent assay surface, a standard curve showing a correlation of the quantity of MRP8/14 with appendicitis severity and/or at least one MRP8/14 standard.

This invention further provides a standard sample comprising a quantity of MRP8/14 corresponding to a quantity of MRP8/14 known to be present in samples from patients having a known appendicitis grade. The invention also comprises a set of standard samples each comprising a quantity of MRP8/14 known to be present in samples from patients having a known appendicitis grade, wherein each standard sample in the set comprises a different quantity of MRP8/14. Each standard sample in the set can comprise a plurality of pooled samples from patients having the same known appendicitis grade. The standard samples can originate from patients or can be synthetic samples comprising quantities of MRP8/14 known to correlate with a set of appendicitis grades. A set of standard samples can comprise at least two samples (each, of course, having a quantity of MRP8/14 correlated with a different appendicitis grade, or at least three or at least four such samples.

This invention also provides a standard curve or data set including a data set in an electronic storage medium comprising data representative of MRP8/14 quantities correlated with appendicitis grades for which said quantities are diagnostic. The electronic storage medium can be in a computer processor, or a CD, disc, tape, DVD or other storage medium known to the art.

This invention further provides a method of scoring the severity of appendicitis corresponding to histological condition of tissue of a patient suspected of suffering from appendicitis. The method comprises examining tissue of the appendix and optionally tissue adjacent thereto from the patient and assigning grade scores to describe the severity of appendicitis in the patient corresponding to the following condition of the tissue. The AppyScore™ grading system is especially useful for this purpose. It is defined as follows: Grade 1: No identifiable inflammation in appendix tissue; Grade 2: Inflammation extending through the mucosa and into the submucosa of the appendix; Grade 3: Inflammation extends past the submucosa into the muscular levels of the appendix; Grade 4: All layers of the appendix, including the serosa, inflamed, and perforation identified.

Anti-MRP8/14 antibodies can be used to detect and quantitate (by the use of comparison with standard samples or a standard curve) the presence of MRP8/14 in patient samples. The presence of MRP8/14 in the sample can be analyzed at a high sensitivity and precision and with a high specificity in a simple manner by the use of anti-MRP8/14 monoclonal antibodies in conventional immunoassay formats, such as enzymatic immunoassays EIA), enzyme-linked immunosorbent assays (ELISA), radioimmunometric assays (RIA), immunoturbidimetric assays, or others known in the prior art. The lab manual by Harlow et al. (1988) discusses many of these methods. The assay comprises immunochemical reagents for forming an immunoreaction product whose presence or amount relates, either directly or indirectly, to the presence or amount of MRP8/14 in the sample. While exemplary assay methods are described herein, the invention is not so limited. Various heterogeneous and homogenous protocols, either competitive or noncompetitive, can be employed in performing an assays of this invention.

For example, anti-MRP8/14 monoclonal antibodies can be used in a direct solid phase immunoassay of the antigen present in a patient sample under conditions where the results are compared to a standard curve based on known amounts of antigen. Furthermore, soluble MRP8/14 antigen present in known amounts of patient specimens can be detected and quantitated either directly or after an initial concentration step by determining the amount of this material required to provide inhibition of antibody binding to immobilized antigen. In these procedures, the patient sample is combined with anti-MRP8/14 antibody and incubated for a period of time sufficient to allow antibody immunocomplexes to form with the soluble antigen. The resulting mixture is incubated with immobilized antigen and the amount of antibody binding to the immobilized antigen determined. The concentration of antigen present in the specimen is determined by comparison to the effect with known amounts of MRP8/14-containing soluble fractions in either single determinations or in serial dilutions of the sample. The dilution state required to relieve the inhibition of binding to the immobilized antigen to a proscribed level would be proportional to the concentration of MRP8/14 present in the sample.

In another illustrative embodiment, a double antibody or "sandwich" immunoassay format is employed comprising the steps of (a) forming a first immunoreaction admixture by admixing a sample with a first (capture) antibody, e.g., a monoclonal antibody, wherein the antibody and MRP8/14 present in the sample are capable of forming a first immunoreaction product (the first antibody can be operatively linked to a solid matrix); (b) maintaining the first immunoreaction admixture so formed under biological assay conditions for a time period sufficient to form the first immunoreaction product (the first immunoreaction product can then be separated from the sample); (c) forming a second immunoreaction admixture by admixing the first immunoreaction product with a second (detection) antibody, monoclonal or polyclonal, which recognizes MRP8/14; (d) maintaining the second immunoreaction admixture so formed under biological assay conditions for a period sufficient to form the second or "sandwich" immunoreaction product; and (e) determining the presence and, optionally, the amount of second immunoreaction product formed, and thereby the presence and the amount of MRP8/14 in the sample. Preferably, the second antibody is labeled, preferably with an enzyme, and thus the second immunoreactions product formed will be a labeled product to facilitate determination of the second immunoreaction product.

In preferred double antibody assay methods, the amount of immunoreaction product determined is related to the amount of immunoreaction product similarly formed and determined using a standard sample in place of the patient sample wherein the standard sample contains a known amount of MRP8/14 in accordance with this invention. Alternatively, a synthetic secondary standard can be used, such as by adding known amounts of MRP8/14 to a suitable carrier, such as buffer, plasma, serum, or the like. The second antibody should be directed to a site on the MRP8/14 which is not the same as the site to which the first antibody is directed.

In any of the illustrative assays, the patient sample can be provided as a known or unknown quantity of blood, or a blood-derived product such as serum or plasma. The amount of antibody used can be known or unknown. The admixture is maintained under biological assay conditions for a predetermined period of one hour or less in embodiments of this invention, at a temperature of from about 4° C. to about 37° C., most preferably about 22° C.

Biological assay conditions are those that maintain the biological activity of the immunochemical reagents of this invention and the MRP8/14. Those conditions can generally include a temperature range of from about 4° C. to about 37° C., a pH value range of from at least about 6.0 to about 8.0, with a preferred range of 7.0 to 7.4, and an ionic strength varying from about 50 mM to 500 mM. Upon routine experimentation, other biological assay conditions may be learned. Methods for optimizing such conditions are well known to those skilled in the art.

Many other types of assays within the scope of this invention will be readily apparent to those skilled in the art.

Also, anti-MRP8/14 antibodies may form part of a kit comprising these antibodies and a means for detecting an immunoreaction product comprising MRP8/14 and the antibody. Instructions for use of a packaged immunochemical reagent are also typically included in such a kit.

As used herein, the term "packaged" can refer to the use of a solid matrix or material such as glass, plastic, paper, fiber, foil and the like capable of holding within fixed limits an antibody of this invention. Thus, for example, a package can be a glass vial used to contain milligram quantities of antibody of the present invention, or it can be a microtiter plate well to which microgram quantities of a contemplated antibody have been operatively affixed. Alternatively, a package could include antibody-coated microparticles entrapped within a porous membrane or embedded in a test strip or dipstick, etc. Alternatively, the antibody can be directly coated onto a membrane, test strip or dipstick, etc. which contacts the sample fluid. Many other possibilities exist and will be readily recognized by those skilled in this art.

Instructions for use typically include a tangible expression, e.g., on paper or electronically encoded on a suitable medium, describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing an antibody of the present invention.

The word "immunocomplex" as used herein refers to the product of a specific binding reaction such as an antibody-antigen or receptor-ligand reaction. Exemplary immunocomplexes are immunoreaction products.

As used herein, the terms "label" and "indicating means" in their various grammatical forms refer to single atoms and molecules that are either directly or indirectly involved in the production of a detectable signal to indicate the presence of an immunocomplex. Any label or indicating means can be linked to or incorporated in an expressed protein, peptide, or antibody molecule that is part of the present invention, or used separately, and those atoms or molecules can be used alone or in conjunction with additional reagents. Such labels are themselves well known in the diagnostic art.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-diethylamine-1-natpthalene-sulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca (1982).

The indicating group may also be an enzyme such as horseradish peroxidase (HRP), glucose oxidase, or the like. In such cases where the principle indicating group is an enzyme such as HRP or glucose oxidase, additional reagents are required to indicate that a receptor-ligand complex (immunoreacant) has formed. Such additional reagents for HRP include hydrogen peroxide and an oxidation dye precursor such as diaminobenzidine. An additional reagent useful with glucose oxidase is 2,2,-azino-di-(3-ethyl-benzthiazoline-G-sulfonic acid) (ABTS).

Radioactive elements are also useful labeling agents and may be used in practicing the present invention. An exemplary radiolabeling agent is a radioactive element that produces gamma ray emissions. Elements which themselves emit gamma rays, such as $^{124}$I, $^{125}$I, $^{128}$I, $^{132}$I, and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. Also useful is a beta emitter, such as $^{111}$In or $^3$H.

The linking of labels, i.e., labeling of peptides and proteins, is well known in the art. For instance, monoclonal antibodies produced by a hybridoma can be labeled by metabolic incorporation of radioisotope-containing amino acids provided as a component in the culture medium. See, for example, Galfre et al. (1981). The techniques of protein conjugation or coupling through activated functional groups are also applicable. See, for example, Aurameas et al. (1978); Rodwell et al. (1984); and U.S. Pat. No. 4,493,795.

The diagnostic test kit can also include, preferably as a separate package, a "specific binding agent," which is a molecular entity capable of selectively binding an anti-MRP8/14 antibody or a complex containing such a species, but is not itself an antibody of this invention. Exemplary specific binding agents are second antibody molecules, including anti-idiotypic antibodies, complement, proteins or fragments thereof. In an embodiment, the specific binding agent binds the antibody when it is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a complex.

The diagnostic kits of the present invention can be used in an ELISA format to detect the quantity of MRP8/14 in patient samples "ELISA" refers to an enzyme linked immunosorbent assay such as those discussed above, which employ an antibody or antigen bound to a solid phase and an enzyme-antigen or enzyme-antibody conjugate to detect and quantify the amount of an antigen present in a sample. A description of the ELISA technique is found in Harlow et al. (1988).

Thus, in preferred embodiments a monoclonal antibody with specificity for MRP8/14 can be affixed to a solid matrix to form a solid support. A reagent is typically affixed to a solid matrix by adsorption from an aqueous medium, although other modes of affixation applicable to proteins and peptides well known to those skilled in the art can be used.

Useful solid matrices are also well known in the art. Such materials are water insoluble and include the cross-linked dextran available under the trademark SEPHADEX (Pharmacia Fine Chemicals, Piscataway, N.J.); agarose; polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The immunoreagents of any diagnostic system described herein can be provided in solution, as a liquid dispersion or as a substantially dry powder, e.g., in lyophilized form. Where the indicating means is an enzyme, the enzyme's substrate can also be provided in a separate package. A solid support such as the above-described microtiter plate and one or more buffers can also be included as separately packaged elements in the diagnostic assay systems of this invention.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

EXAMPLES

Example 1

MRP8/14

The objective of this study was to identify a tissue-specific marker that could contribute to the decision matrix for diagnosing early acute appendicitis. A proteomic screen was used to identify a protein in the appendix specifically upregulated in acute appendicitis. MRP8/14 was identified as present both in the diseased appendix and in serum of acute appendicitis patients.

MATERIALS AND METHODS. Specimen and Serum Collection. All patients enrolled in this study were treated according to accepted standards of care as defined by their treating physicians. Prior to being approached for inclusion in our study, all patients were evaluated by a surgeon and diagnosed by that surgeon as having appendicitis. The treating surgeon's plans for these appendicitis patients included an immediate appendectomy. The specifics of all treatments such as use of antibiotics, operative technique (either open or laparoscopic) were determined by the individual surgeon.

Exclusion Criteria: Any patients with pre-existing chronic inflammatory diseases such as asthma, rheumatoid arthritis, inflammatory bowel disease, psoriasis, or neutropenia. Pregnancy was also considered an exclusion criterion.

An investigator counseled all patients about the study and informed consent was obtained. At the time of informed consent, the subject was assigned an identification number and non-personal demographic and clinical information was obtained (age, sex, race, duration of symptoms, white blood count (WBC), results of imaging studies, etc).

At the time of surgery, following induction of general anesthesia, a whole blood sample (5-10 cc volume) was obtained via peripheral venopuncture. This blood specimen was then placed on ice. As soon as possible, a small sample (approximately 1 gram) of inflamed appendix was taken from the pathologic specimen and also placed on ice. The iced blood specimens were then centrifuged for 20 minutes at 3000 rpm and the separated serum isolated. This isolated serum and the piece of appendix tissue were then stored separately, frozen at −80° C.

Appendicitis Tissue Processing. Appendix tissue from appendectomy patients was harvested and stored at −80° C. until processed. Individual tissue samples were ground into powder using a sterile mortar and pestle under liquid nitrogen. Protein was extracted from tissue powder by incubating at 37° C. in Extraction Buffer (0.025M Tris-base, 200 mM Sodium Chloride, 5 mM EDTA, 0.1% Sodium Azide, pH 7.5). Samples were centrifuged for 10 minutes at 14K rpm. Supernatants were stored at −80° C. until analysis.

2D Gel Analysis of Extracted Tissue Samples. 2D gel analysis was performed on depleted serum samples and extracted tissue samples. Isoelectric focusing (IEF) and SDS-PAGE were performed according to the Zoom (Invitrogen) protocol for 2D Gel analysis. Equal quantities of protein were analyzed on each gel. Comparisons between negative serum gel and positive serum gel were made to determine which proteins were present in positive samples and absent in negative samples. Candidate gel spots were identified and submitted to MALDI-TOF protein identification analysis (Linden Biosciences).

Western Blot Analysis of Extracted Appendix Tissue Samples. Samples (10 pg) were subjected to standard Laemmli SDS-PAGE and proteins were transferred to nitrocellulose membrane for western blot analysis using standard techniques with chemiluminescent detection. Magic Mark Western Standard (Invitrogen) was used to determine molecular weight. MRP8 (Calgranulin A C-19, Santa Cruz, SC-8112) was used in a 1:100 dilution in 0.5×Uniblock (AspenBio Pharma, Inc) for primary antibody. The secondary antibody was Peroxidase anti-goat IgG (H+L), affinity purified (Vector, PI-9500) in a 1:2000 dilution in Uniblock. MR-14 (Calgranulin B C-1 9, Santa Cruz, SC-8114) was used in a 1:100 dilution in 0.5×Uniblock for primary antibody. The secondary antibody was Peroxidase anti-goat IgG (H+L), affinity purified (Vector, PI-9500) in a 1:2000 dilution in Uniblock.

Serum MRP8/14 Determinations. Serum levels of MRP8/14 were determined by ELISA using a commercially available ELISA (Buhlmann S100-Cellion S100 A8/A9) according to the manufacturer's protocol.

RESULTS. Identification of Proteins Present in Appendix Tissue from Appendicitis Patients. A differential proteomic analysis was performed on depleted serum samples with the goal of identifying proteins elevated in patients with acute appendicitis. The analysis involved comparing samples from normal patients versus patients with perforated appendices. Blood samples were obtained immediately prior to surgery. A normal patient in this study is one that presented with abdominal pain, underwent surgery, and was found to have a normal appendix. Normal and diseased appendix tissue was collected during surgery.

Figure 1B:
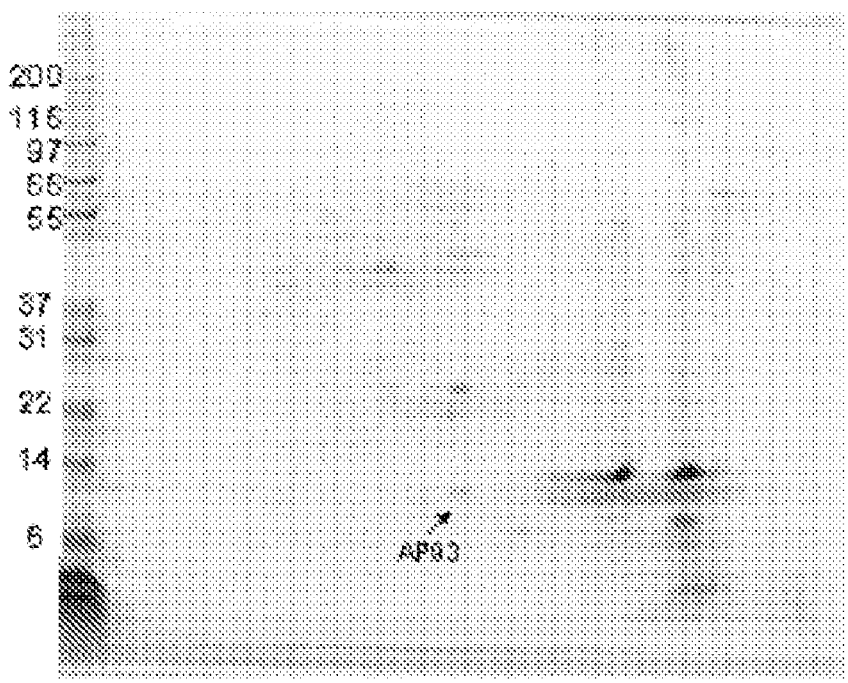

The proteomic approach was to compare a pool of 4 normal samples with a pool of 4 appendicitis samples using two-dimensional electrophoresis. FIG. 1 shows the 2D profile of proteins analyzed. Comparison between the gels was performed and the most obvious difference is indicated in FIG. 1B as AP-93. Based on the gel in FIG. 1, the molecular weight of AP-93 is approximately 14 kilodaltons. The corresponding gel slice was analyzed by MALDI-TOF and a positive identification was made. The identification was based upon spectra of two tryptic peptides, NIETIINTFHQYSVK [SEQ ID NO:3] and LGHPDTLNQGEFKELVR [SEQ ID NO:4]. The peptides correspond to the underlined residues in the following amino acid sequence of MRP14 (GenBank Accession Number P06702):

[SEQ ID NO: 5]
MTCKMSQLE<u>RNIETIINTFHQYSVK</u><u>LGHPDTLNQGEFKELVR</u>KDLQNFLK

KENKNEKVIEHIMEDLDTNADKQLSFEEFIMLMARLTWASHEKMHEGDEG

PGHHHKPGLGEGTP.

The MALDI-TOF identification of AP-93 as MRP14 was confirmed by the matching molecular weights. Based on this data, MRP14 protein was more highly abundant in the diseased sample pool than in the normal sample pool.

Figure 2:
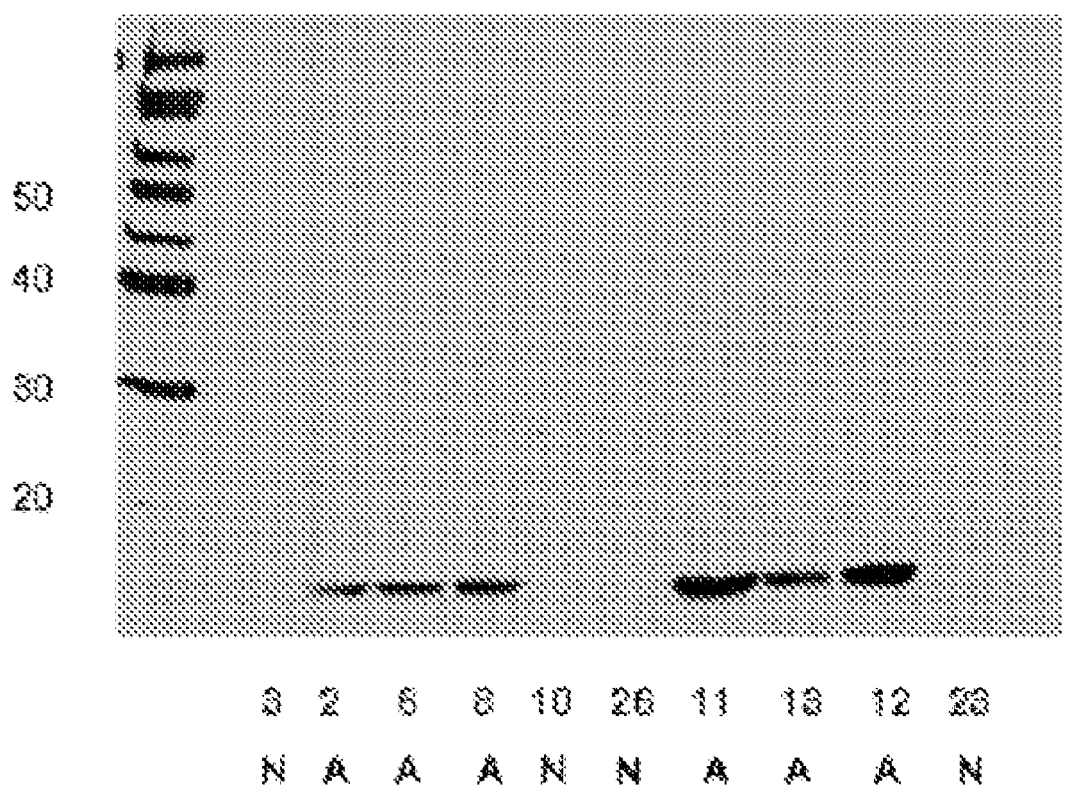
FIG. 2: MRP14 western blot analysis of normal (N) and diseased (A) appendix tissue. The numbers are sample ID numbers. Molecular weights are shown in kilodaltons.

Presence of MRP14 and MRP8 in Diseased Appendix Tissue. In order to confirm the presence of MRP14 in diseased tissue, an anti-MRP14 antibody was used in western blotting of tissue extracts from individual normal and diseased appendices. FIG. 2 shows the western blot data from 9 normal and 11 appendicitis samples. A 14 kilodalton band is present in every appendicitis sample. There is no detectable signal in the normal samples. This data confirms the proteomic screen data and shows that the protein is an indicator of diseased appendix tissue.

Figure 3:
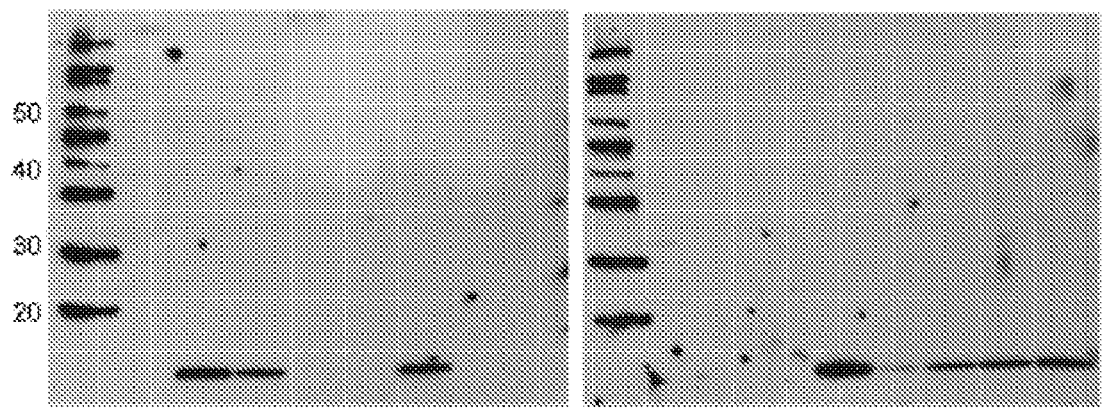
FIG. 3: MRP8 western blot analysis of normal (N) and diseased (A) appendix tissue. The numbers are sample ID numbers. Molecular weights are shown in kilodaltons.
Figure 4:
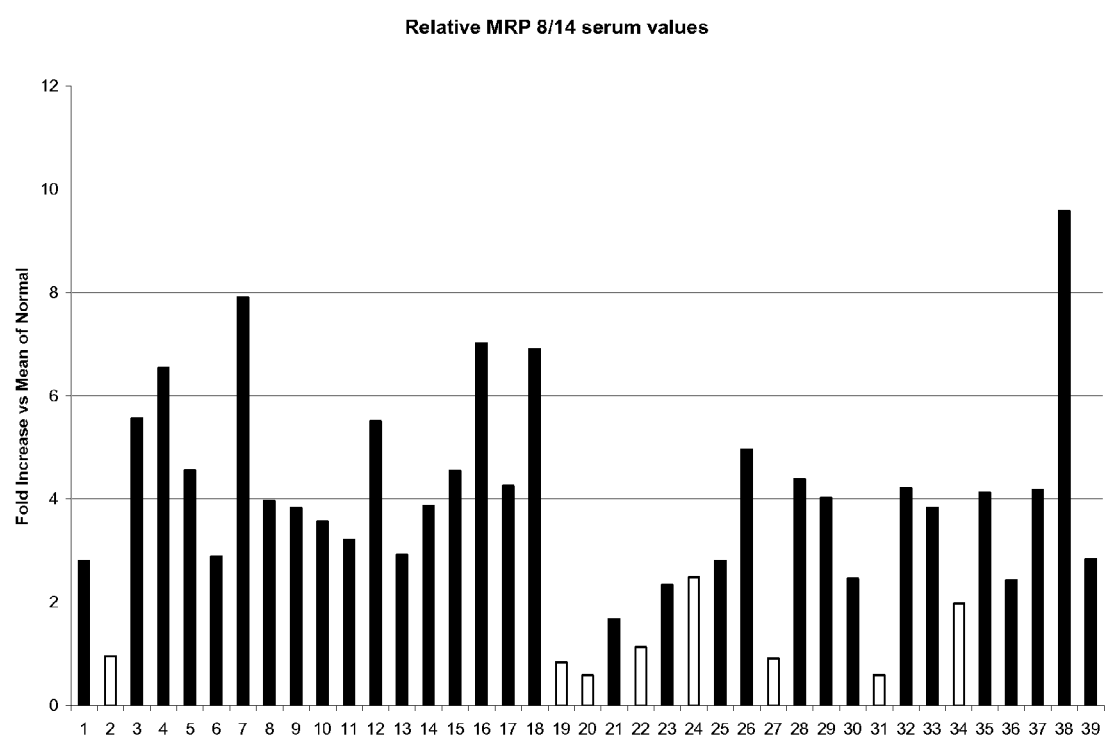
FIG. 4: Relative levels of MRP8/14 in normal and appendicitis serum as determined by ELISA. The levels are given as a fraction of the mean for the patients not having appendicitis, said fraction also being referred to herein as a "fold increase." Dark bars represent samples from patients having appendicitis. White bars represent samples from patients not having appendicitis.

Since it is known that MRP8 exists as a dimer with MRP14, tissue specimens were also examined for the presence of MRP8. FIG. 3 shows the western blot data using an anti-MRP8 antibody on the normal and diseased tissue samples. As expected, MRP8 is present in all of the diseased appendix samples and not detectable in the normal appendix tissue. These western blot data show that the MRP8 and MRP14 proteins are markedly more abundant in appendicitis than in normal appendix tissue.

Elevated Serum Levels of MRP8/14 Patients with Acute Appendicitis. The high correlation between appendicitis and the presence of MRP8/14 in the appendix led us to examine the MRP8/14 levels in serum of those patients and other patients subsequently added to the study. The sera were collected before surgery, banked and analyzed after the disease status was known. MRP8/14 levels were measured using a sandwich ELISA specific for the complex.

Table 1 lists serum MRP8/14 levels for 39 patients as determined by an ELISA manufactured by Hycult (Netherlands) and available commercially through Cell Sciences, Canton, Mass. The amounts are given as fractions compared to an average level for patients in the study without appendicitis. Note that all patients with appendicitis show a fold-increase of MRP8/14 over average normal levels. The procedure was conducted according to instructions accompanying the ELISA product. The sample numbers do not correspond to the sample numbers shown in FIGS. 2 and 3 as the samples were renumbered.

TABLE 1

| Sample Number | Clinical Diagnosis | Pathology | Grading | Fraction of Normal |
|---|---|---|---|---|
| 1 | Advanced Appendicitis | Mild Acute Appendicitis | 2 | 2.80428 |
| 2 | Normal Appy | Normal | 1 | 0.960805 |
| 3 | Advanced Appendicitis | Transmural Appendicitis | 3 | 5.554904 |
| 4 | Perforated Appy | Perforated Appy-Necrosis | 4 | 6.53913 |
| 5 | Early Appy | Mild Acute Appendicitis | 2 | 4.562059 |
| 6 | Early Appy | Mild-Acute Appendicitis | 1 | 2.881124 |
| 7 | Horrible perforated | Perforated Appy-Necrosis | 4 | 7.906886 |
| 8 | Normal Appy | Mild Acute Appendicitis | 2 | 3.971489 |
| 9 | Early Appy | Transmural Appendicitis | 3 | 3.83328 |
| 10 | Advanced Appendicitis | Transmural Appendicitis | 3 | 3.566665 |
| 11 | Appendicitis | Mild Acute Appendicitis | 2 | 3.205335 |
| 12 | Appendicitis | Transmural Appendicitis | 3 | 5.51224 |
| 13 | Advanced Appendicitis | Transmural Appendicitis | 3 | 2.92671 |
| 14 | Advanced Appendicitis | Transmural Appendicitis w Necrosis | 4 | 3.866306 |
| 15 | PERFORATED | Transmural Appendicitis | 3 | 4.54657 |
| 16 | Advanced Appendicitis | Perforated Appy | 4 | 7.01877 |
| 17 | Advanced Appendicitis | Transmural Appendicitis | 3 | 4.25998 |
| 18 | Appendicitis | Transmural Appendicitis | 3 | 6.90312 |
| 19 | Normal Appy | Normal | 1 | 0.838679 |
| 20 | Normal Appy | Normal | 1 | 0.590095 |
| 21 | Early Appy | Appendicitis with Peri appy changers | 3 | 1.682291 |
| 22 | Normal Appy | Normal | 1 | 1.128849 |
| 23 | Advanced appendicitis | Transmural Appendicitis | 4 | 2.338583 |
| 24 | Normal Appy | Normal | 1 | 2.478035 |
| 25 | Hot appy | | | 2.807046 |
| 26 | Perforated | Perforated | 4 | 4.954136 |
| 27 | Normal | Normal | 1 | 0.918438 |
| 28 | Hot | Hot | 2 | 4.387589 |
| 29 | Early | Transmural Appendicitis | 3 | 4.015013 |
| 30 | Hot | Transmural Appendicitis | 3 | 2.460902 |
| 31 | Normal | Normal | 1 | 0.594943 |
| 32 | Hot | Transmural Appendicitis | 3 | 4.211086 |
| 33 | Perforated | Transmural Appendicitis | 4 | 3.835219 |
| 34 | Normal | Normal | 1 | 1.968859 |
| 35 | Perforated | Transmural Appendicitis | 4 | 4.126198 |
| 36 | Advanced | Transmural Appendicitis | 3 | 2.423726 |
| 37 | Hot Appy | Transmural Appendicitis | 3 | 4.178647 |
| 38 | Early | Transmural Appendicitis | 3 | 9.584398 |
| 39 | Normal | Transmural Appendicitis | 2 | 2.835339 |

We have identified a protein complex that is present in the appendix and serum of appendicitis patients. Based on the western blot data, the presence of MRP8/14 in appendix tissue is highly correlative with disease. Furthermore, levels of MRP8/14 in serum are predictive of appendicitis. We presume that this increase is due to increased production of these proteins from systemic neutrophil infiltration of the appendix and possibly direct mucosal production of the proteins by the appendix itself. This study demonstrates that MRP8/14 is a useful clinical marker for acute appendicitis. After our discovery that MRP8/14 was a molecule differentially associated with appendicitis, our work was confirmed by the finding of Power, C. et al., 2004 and 2005, who reported detection of this molecule in feces of patients having acute appendicitis.

Example 2

Haptoglobin

Using a proteomic screen of serum and appendix tissue, we determined that haptoglobin is upregulated in patients with acute appendicitis. The alpha subunit of haptoglobin is an especially useful marker in screening for the disease.

MATERIALS AND METHODS. Specimen and serum collection, appendicitis tissue processing, 2D gel analysis of extracted tissue samples, and western blot analysis of extracted appendix tissue samples were as described above in Example 1, except that for the western blot, affinity-purified anti-human haptoglobin (Rockland, 600-401-272) was used at a 1:5000 dilution in 0.5×uniblock for the primary antibody; and the secondary antibody was peroxidase anti-rabbit IgG (h+1), affinity purified (vector, pi-1000) in a 1:5000 dilution in uniblock.

RESULTS. Identification of proteins present in appendix tissue from appendicitis patients. A differential proteomic analysis was performed on depleted serum samples with the goal of identifying proteins elevated in patients with acute appendicitis. The analysis involved comparing samples from normal patients versus patients with perforated appendices. Blood samples were obtained immediately prior to surgery. A normal patient in this study is one that presented with abdominal pain, underwent surgery, and was found to have a normal appendix. Normal and diseased appendix tissue was collected during surgery.

Figure 5A:
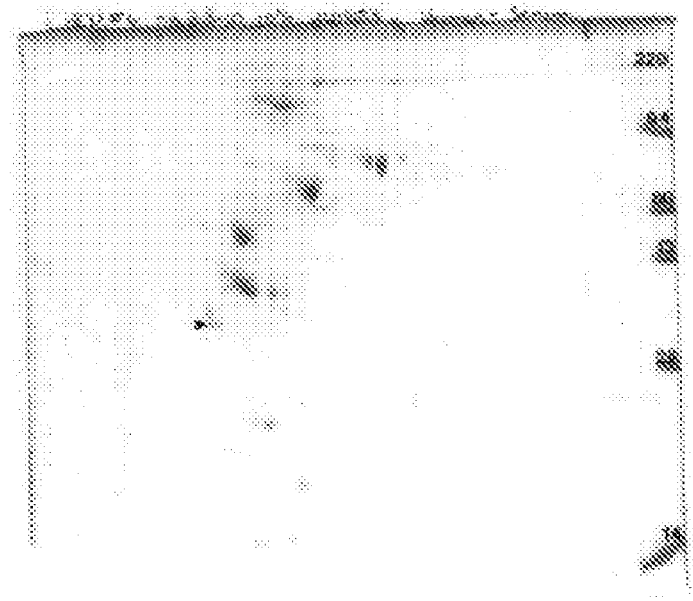
FIG. 5: Two-dimensional electrophoresis image of proteins in depleted serum samples from (A) normal and (B) appendicitis patients. Proteins were separated by isoelectric focusing on the x-axis and by molecular weight on the y-axis. The molecular weight in kilodaltons is shown in the right. The tailed arrow indicates the upregulated protein, AP-77 (haptoglobin alpha subunit). The untailed arrow indicates a control protein that is equally abundant in diseased vs. normal.
Figure 5B:
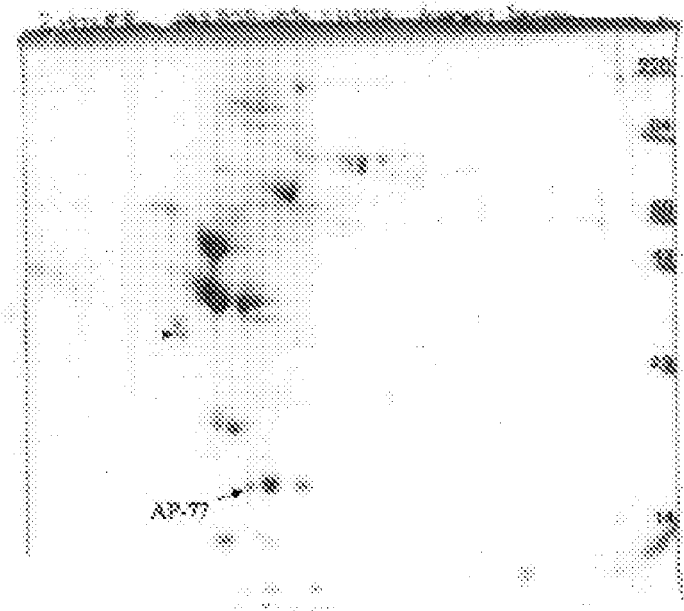

The proteomic approach was to compare a pool of 4 normal samples with a pool of 4 appendicitis samples using two-dimensional electrophoresis. FIG. 5 shows the 2D profile of proteins analyzed from serum depleted of IgG and albumin. Comparison between the gels was performed and the most obvious difference is indicated in FIG. 5B as AP-77. The protein in gel spot AP-77 was digested with trypsin and analyzed by MALDI-TOF. The resulting two peptides have the following sequences: TEGDGVYTLNNEKQWINK [SEQ ID NO:6] and AVGDKLPECEADDGCPKPPEIAHGYVEHSVR [SEQ ID NO:7]. The sequences were aligned with the alpha subunit of haptoglobin. The sequence of haptoglobin precursor (Gen-Bank Accession Number NP005134) is shown below with the tryptic fragments underlined.

[SEQ ID NO: 8]
MSALGAVIALLLWGQLFAVDSGNDVTDIADDGCPKPPEIAHGYVEHSVRY

QCKNYYKLRTEGDGVYTLNDKKQWINKAVGDKLPECEADDGCPKPPEIAH

GYVEHSVRYQCKNYYKLRTEGDGVYTLNNEKQWINKAVGDKLPECEAVCG

KPKNPANPVQRILGGHLDAKGSFPWQAKMVSHHNLTTGATLINEQWLLTT

AKNLFLNHSENATAKDIAPTLTLYVGKKQLVEIEKVVLHPNYSQVDIGLI

KLKQKVSVNERVMPICLPSKDYAEVGRVGYVSGWGRNANFKFTDHLKYVM

-continued
LPVADQDQCIRHYEGSTVPEKKTPKSPVGVQPILNEHTFCAGMSKYQEDT

CYGDAGSAFAVHDLEEDTWYATGILSFDKSCAVAEYGVYVKVTSIQDWVQ

KTIAEN.

Figure 6A:
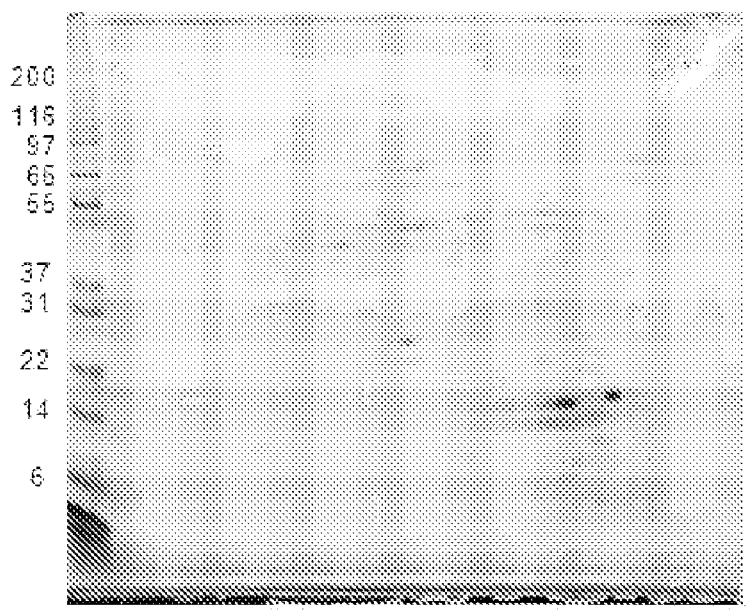
FIG. 6: Two-dimensional electrophoresis image of proteins from (A) normal and (B) diseased (perforated) appendix tissue. Proteins were separated by isoelectric focusing on the x axis and by molecular weight on the y axis. The molecular weight in kilodaltons is shown on the left. The arrow indicates the upregulated protein, AP-91 (haptoglobin alpha subunit).
Figure 6B:
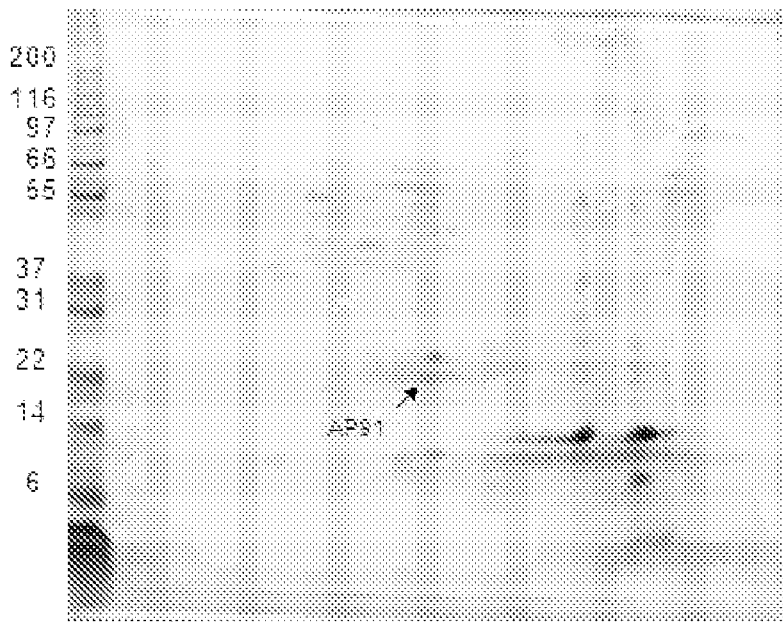
Figure 9:
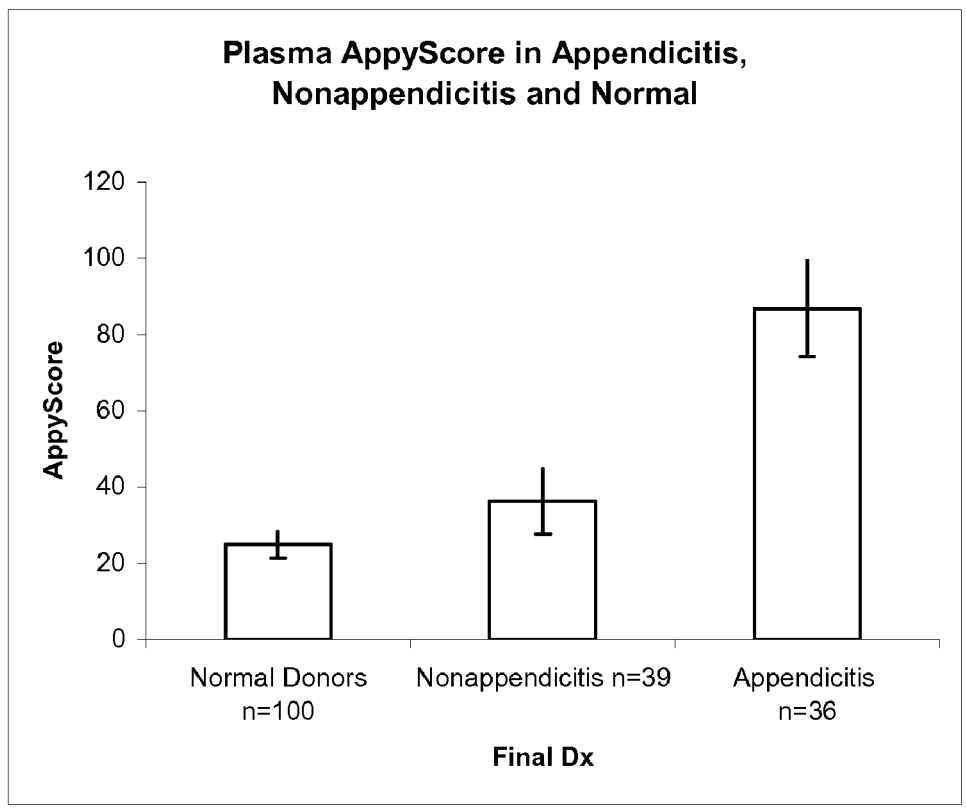
FIG. 9: Average (±SEM) AppyScore™ Values from normal, nonappendicitis with lower right-quadrant pain, and appendicitis patients.
Figure 10:
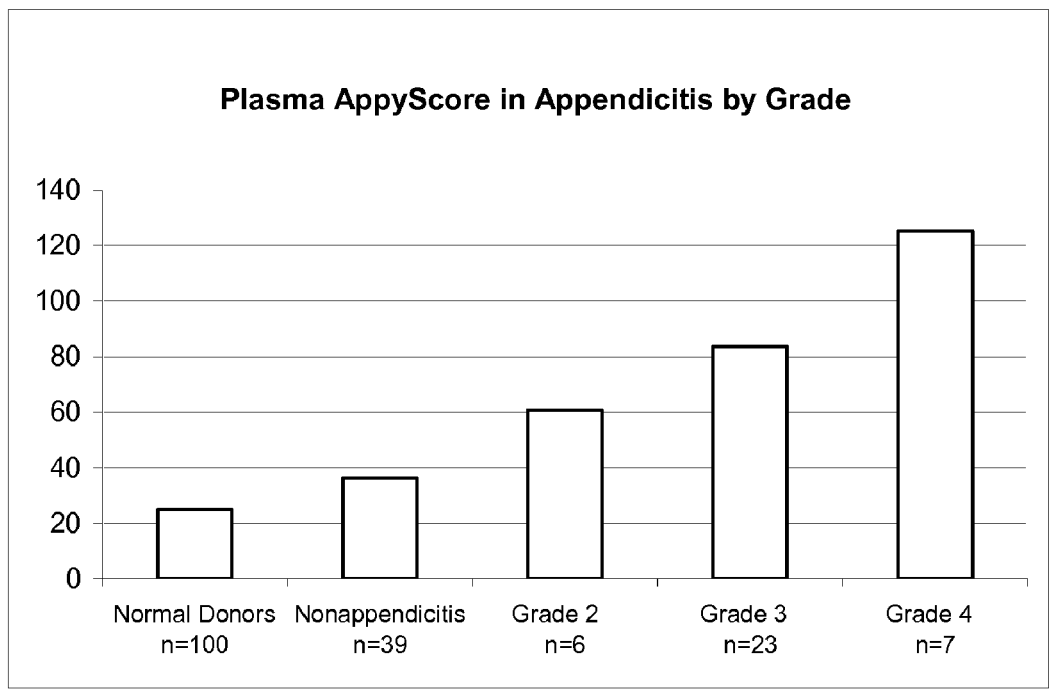
FIG. 10: Average AppyScore™ Values from normal, non-appendicitis with lower right-quadrant pain, and appendicitis patients. The appendicitis cases are categorized by histopathological grade.
Figure 11:
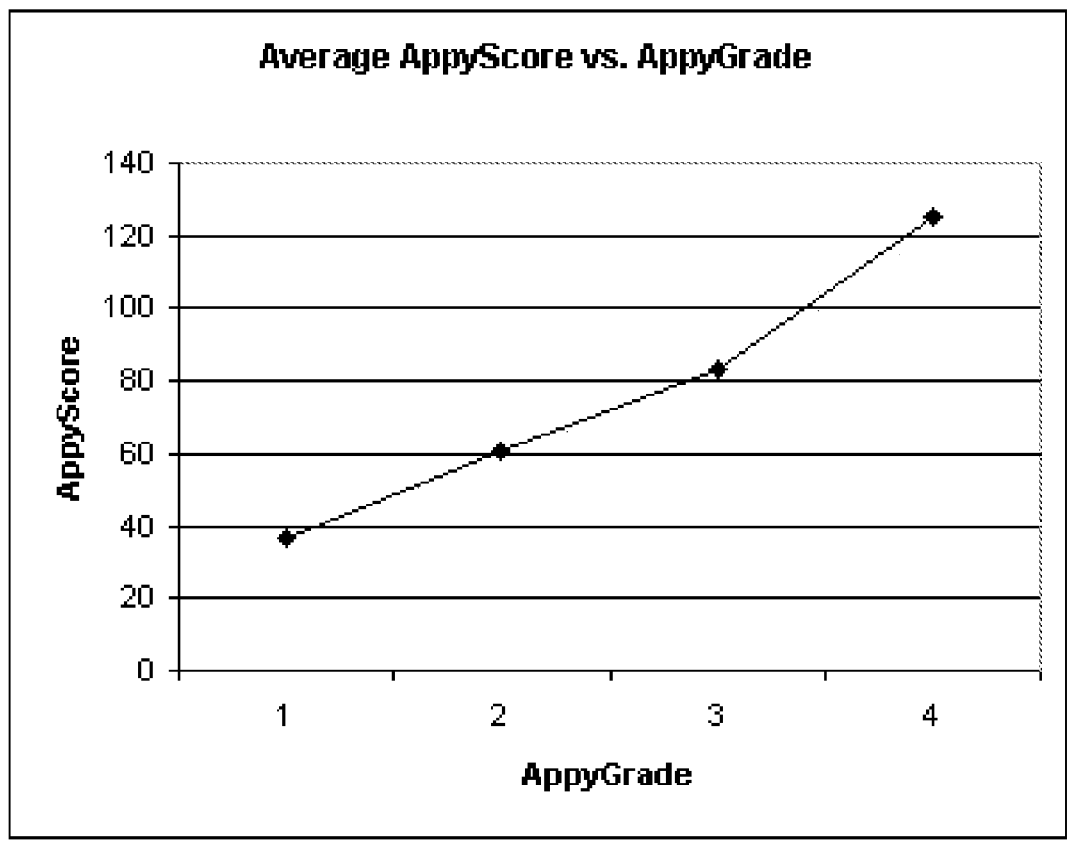
FIG. 11: Standard curve for use in assigning AppyScore™ values to patient specimens.

FIG. 6 shows the two-dimensional electrophoresis profile comparison between diseased and normal appendix tissue proteins. Two spots, AP-91 and AP-93, were analyzed by MALDI-TOF and positive identifications were determined. AP-91 protein was determined to be identical to AP-77, haptoglobin-alpha Elevated haptoglobin in diseased appendix tissue. In order to confirm the presence of haptoglobin in diseased tissue, an anti-haptoglobin antibody was used in western blotting of tissue extracts from individual normal and diseased appendices. FIG. 7 shows the western blot data from 6 normal and 6 appendicitis samples. Nearly every sample contained some level of the 38 kd beta subunit, however, there appeared to be an elevated level in cases of appendicitis. A >20 kilodalton band is present in every appendicitis sample and absent from all of the normal tissue samples. This data confirms the proteomic screen data and shows that the protein is an indicator of diseased appendix tissue. The alpha subunit has higher specificity than the beta subunit.

Example 3

Method of Identifying Molecules using Fluid Samples

In variations of this example, fluid samples can include whole blood, serum, or plasma. The samples were whole blood collected from human patients immediately prior to an appendectomy. The specimens were placed on ice and transported to the lab. The blood was then processed by centrifugation at 3000 rpm for 15 minutes. Plasma was then separated by pouring into another container Upon performing an appendectomy, a patient was classified as having appendicitis (AP) or non-appendicitis (NAP). The classification was based on clinical evaluation, pathology, or both as known in the art. For cases of appendicitis, the clinical condition was also characterized as either perforated or non-perforated.

The samples from AP patients were pooled and divided into aliquots. Pooled aliquots were treated so as to remove selected components such as antibodies and serum albumin. Similarly, the samples from NAP patients were pooled and divided into aliquots with treatment to remove the same selected components. the AP samples and NAP samples were processed in a similar manner.

Next, the pooled aliquots of AP and NAP samples were each subjected to two-dimensional gel electrophoresis as known in the art. The results of each sample type were compared with respect to the presence, absence, and relative expression levels of proteins. Signals corresponding to proteins derived from AP samples were detected that were either absent or expressed at relatively lower levels in NAP samples. Further characterization was performed for such AP proteins.

The further characterization includes partial amino acid sequencing, mass spectrometry, and other analytical techniques as known in the art. A full length clone of the gene corresponding to the partial amino acid sequence can be isolated and expressed as a recombinant protein. The recombinant protein was used as an antigen for detection. Alternatively, a partial or complete recombinant protein can be used to induce or otherwise generate a specific antibody reagent, polyclonal or monoclonal. The antibody reagent was used in the detection of antigen in a patient so as to aid in appendicitis diagnosis. A combination of antigenic molecules can be employed in appendicitis diagnosis.

Example 4

Gene Chip Screen for Identification of Proteins in Patient Tissue Samples

In this example, a gene chip screen was employed to identify candidate molecules differentially associated with the condition of appendicitis.

Tissue Description. Appendices were removed from human donors undergoing appendectomies as a result of positive appendicitis diagnosis (pending pathology of surgically removed appendices). Donors were divided into two groups, "normal" and "appendicitis", based on pathology findings. The appendicitis group consisted of patients ranging in age from 7 to 13 years, and the normal group consisted of patients ranging in age from 8 to 19 years.

RNA Extraction. Tissue was stored at −80° C. until processing. Approximately 2 grams of frozen human appendix tissue from each of eight donors were ground under liquid nitrogen using a mortar and pestle. Approximately 100 mg of appendix powder from each patient was pooled according to diagnosis (normal and appendicitis). Total RNA was extracted from approximately 100 mg of pooled tissue powder using an RNeasy Kit (Qiagen Inc., Valencia, Calif.) according to the manufacturer's instructions.

Differential Expression Analysis. Differential cDNA expression from total RNA was performed by a service provided by the University of Colorado Health Sciences Center Microarray Core Facility (see the microarray.uchsc.edu website). The screen utilized an Affymetrix Chip, HG-U 133 Plus 2 (see the affymetrix.com website). Transcripts having significantly high expression level in appendicitis tissue versus normal tissue were selected for further study.

TABLE 2

Specifications of Affymetrix Gene Chip (U133 Plus 2.0 Array)

| Item | Description |
|---|---|
| Number of arrays in set | 1 |
| Number of transcripts | ~47,400 |
| Number of genes | 38,500 |
| Number of probe sets | >54,000 |
| Feature size | 11 μm |
| Oligonucleotide probe length | 25-mer |
| Probe pairs/sequence | 11 |
| Control sequences included: | |
| Hybridization controls | bioB, bioC, bioD, cre |
| Poly-A controls | dap, lys, phe, thr |
| Normalization control set | 100 probe sets |
| Housekeeping/Control genes | GAPDH, beta-Actin, ISGF-3 (STAT1) |
| Detection sensitivity | 1:100,000* |

*As measured by detection of pre-labeled transcripts derived from human cDNA clones in a complex human background.

From the candidate molecules differentially associated with appendicitis according to the results of the screening, one or more protein molecules corresponding to genes in FIG. 1 are selected for use in a diagnostic assay for appendicitis.

In a further screen, the above gene chip approach is repeated and results are assessed to determine whether there is a correlation between or among gene chip outcomes regarding the fold change value for an individual molecule or for a set of molecules in a given range of fold change values. Molecules having a positive correlation with upregulated fold change values are preferably selected for use in a diagnostic assay for appendicitis.

Example 5

Protein Identification from Tissue Samples (Subtraction Library)

Tissue samples are collected from appendicitis (AP) and non-appendicitis (NAP) patients. Preferably the tissue is the appendix. The AP or NAP tissues samples are optionally pooled so as to generate an AP tissue pool or an NAP tissue pool. The AP and NAP tissue samples are each used as a source for isolation of total RNA and/or mRNA. Upon isolation, the AP-RNA and NAP-RNA are maintained separately and used for preparation of cDNA.

In an alternate procedure to that of Example 4, a subtraction library is created using techniques available in the art. A cDNA library is optionally amplified. The cDNA library is treated so as to remove undesirable constituents such as highly redundant species and species expressed both in diseased and normal samples. Examples of the techniques include those described by Bonaldo et al. (1996) and Deichmann M et al. (2001).

Upon generation of the subtraction library, one analyzes, isolates, and sequences selected clones corresponding to sequences differentially expressed in the disease condition. Using molecular biology techniques, one selects candidates for recombinant expression of a partial or complete protein. Such a protein is then used as an antigen for detection. Alternatively, a partial or complete recombinant protein can be used to induce or otherwise generate a specific antibody reagent, polyclonal or monoclonal. The antibody reagent is used in the detection of antigen in a patient so as to aid in appendicitis diagnosis. It is envisioned that a combination of antigenic molecules can be employed in appendicitis diagnosis.

Example 6

Method of Appendicitis Diagnosis by Evaluation of Plasma Sample Viscosity

Whole blood was drawn from a suspected appendicitis patient immediately prior to appendectomy. The specimens were placed on ice and transported to the clinical lab. The blood was processed by centrifugation at 3000 rpm for 15 minutes followed by separation of plasma from the sample by pouring into another container.

During the step of pouring, the samples were evaluated with respect to viscosity. Increased viscosity is indicative of appendicitis. Approximately 80% of samples corresponding to appendicitis cases demonstrated increased viscosity, whereas approximately none to less than 5% of samples corresponding to non-appendicitis cases demonstrated increased viscosity. It is noted that the degree of increased viscosity correlates with the severity of appendicitis.

Viscosity measurements can be conducted by visual observation or by using techniques known in the art. For example, a Coulter Harkness capillary viscometer can be used (Harkness J., 1963) or other techniques (Haidekker M A, et al., 2002).

The presence of increased viscosity in plasma can be used in combination with other diagnostic techniques, for example with one or more of the following: physical examination, complete blood count (CBC) with or without differential, urinalysis (UA), computed tomography (CT), abdominal ultrasonography, and laparoscopy.

Example 7

MRP8/14 Concentrations

Sample Acquisition. The Institutional Review Boards representing the participating hospitals approved and supervised this study. Selected patients were enrolled from one of five community hospital emergency rooms located in the Denver, Colorado metropolitan area. All patients were complaining of right lower quadrant abdominal pain and in all cases the patient's treating emergency room physician considered the diagnosis of appendicitis in their differential. Patients were excluded from participation if they had a pre-existing medical history that included neutropenia or chronic inflammatory diseases such as rheumatoid arthritis, inflammatory bowel disease, and psoriasis.

After inclusion criteria were met each patient was approached and counseled, by a senior investigator or their representative, prior to obtaining informed consent. Following consent patient demographic data, history and physical information, and the results of any pertinent laboratory or imaging study was collected and stored in an electronic database. Whole blood samples for serum and plasma were then obtained via peripheral venopuncture using standard sterile technique. The whole blood samples were immediately placed on ice and transported to the laboratory for centrifugation. All samples were centrifuged at 3000 rpm for 15 minutes to separate the cellular mass from the serum and plasma. The resultant serum or plasma was poured into a separate test tube and then frozen at −80° C. In cases where appendectomy was performed, a sample of the patient's appendix was obtained in a manner that did not interfere with routine pathologic examination and then stored frozen at −80° C.

Histopathological Grading System for Severity of Appendicitis

A novel grading system was established to describe the severity of inflammation in appendix tissue from appendicitis patients. Grade 1 represents no identifiable inflammation within the appendix. Grade 1 is also used to identify patients that did not have appendicitis and had not undergone appendectomy. Grades 2-4 describe the highest level of inflammation identified within the appendix. If the level of inflammation is contained exclusively within the mucosa of the appendix, although this is classified is Grade 2 chronic, and this level of inflammation is NOT considered consistent with acute appendicitis. In Grade 2 appendicitis, the level of inflammation has extended through the mucosa and reached the sub-mucosa. When the level of inflammation extends past the sub-mucosa and reaches into the muscular levels of the appendix the appendicitis Grade is raised to 3. Finally, Grade 4 is when all the layers of the appendix including the serosa is involved and perforation is identified.

MRP8/14 concentrations by ELISA assay (4 Hour Assay)

Analyses of MRP8/14 in serum and plasma samples were performed using a sandwich ELISA that utilizes monoclonal antibody 27E10 to MRP8/14 (Cell Sciences, Inc., Canton, Mass.) Chicken polyclonal anti-MRP8/14 antibody, and Goat polyclonal anti-Chicken horseradish peroxidase (HRP) antibody on 96-well plates (Nunc, VWR, West Chester, Pa.). Plates were coated with 100 µl of monoclonal 27e10 diluted to 10 µg/ml and incubated overnight at 4° C. Wells were washed 2 times with phosphate buffered saline (1×, pH 7.4) and 0.05% Tween-20 (PBST) and 200 µl of 5% bovine serum albumin in PBST (BSA-PBST) block was added and plates were incubated for 1 hour at 37° C.

The biological serum reference standard was diluted at a 1:100 and two-fold dilution to a 1:6400 dilution in 0.1% BSA-PBST. The biological plasma reference standard was diluted at a 1:25 and two-fold dilution to a 1:1600 dilution also in 0.1% BSA-PBST. MRP8/14 samples and controls were diluted at a 1:100 dilution for plasma and a 1:200 dilution for serum in 0.1% BSA-PBST and 100 µl of each diluted sample, standard, and control was added in triplicate to the plates.

Wells were washed 4 times after incubation of 1 hour at 37° C. and 100 µl of secondary antibody was added to each well at a concentration of 0.3125 µg/ml (Chicken polyclonal anti-MRP8/14, Bachem, San Carlos, Calif.). After incubation of 1 hour at 37° C., wells were washed again and 100 µl of a 1:4000 dilution of detection antibody was added to each well (Goat Polyclonal anti-Chicken HRP, Abcam, Cambridge, Mass.). Wells were washed for the final time after incubation of 1 hour at 37° C. and 100 µl of 3,3',5,5'-tetramethylbenzidine (TMB) substrate was added and incubated at room temperature for 1-5 minutes (TMB Substrate, Sigma, St. Louis, Mo.). Reaction was stopped with 100 µl of 0.18 M Sulfuric Acid.

The intensity of the reaction was measured at 450 nm using a microplate reader. To determine MRP8/14 levels the absorbance measurements of the standard, samples, blanks, and controls were averaged. Next, the standard, sample, and control averages were subtracted from the blank averages to obtain the corrected absorbance. Arbitrary units were assigned to the standard curve dilutions and the natural log of each arbitrary unit was determined. The slope of the standard curve was established by plotting the corrected absorbance (450 nm) versus the natural log of the arbitrary units. MRP8/14 levels were quantified for each sample by interpolating the corrected absorbance with the standard curve and then using the exponential function. Concentrations were expressed in arbitrary units (AppyScore™ value). Raw serum values were converted to AppyScore™ value by multiplying by a factor of 0.4.

MRP8/14 Concentrations by ELISA Assay (60 Minute Assay)

The total test time for the MRP8/14 ELISA was minimized to 1 hour by decreasing each incubation step down to 15 minutes. Optimization of the ELISA for plasma samples was performed using the sandwich ELISA which utilizes monoclonal 27E10, Chicken polyclonal anti-MRP8/14, and Goat polyclonal anti-Chicken HRP on 96-well plates (Nunc, VWR, West Chester, Pa.). Plates were coated with 100 µl of monoclonal 27E10 diluted to 10 µpg/ml and incubated overnight at 4° C. Wells were washed 2 times with 0.05% 1×PBST and 200 µl of 5% BSA-PBST block was added and plates were incubated for 15 minutes at 37° C. on a shaker.

The biological plasma reference standard was diluted at a 1:25 and two-fold dilution to a 1:1600 dilution also in 0.1% BSA-PBST. Plasma samples with known MRP8/14 values were chosen to determine whether the decrease in test time affected MRP8/14 levels. Plasma samples and controls were diluted at a 1:100 dilution in 0.1% BSA-PBST and 100 µl of each diluted sample, standard, and control was added in triplicate to the plates.

Wells were washed 4 times after shaking for 15 minutes at 37° C. and 100 µl of secondary antibody was added to each well at a concentration of 0.31 25 µg/ml (Chicken polyclonal anti-MRP8/14, Bachem, San Carlos, Calif.). After incubation of 15 minutes at 37° C. on a shaker, wells were washed again and 100µl of a 1:4000 dilution of detection antibody was added to each well (Goat Polyclonal anti-Chicken HRP, Abcam, Cambridge, Mass.). Wells were washed for the final time after shaking for 15 minutes at 37° C. and 100 µl of TMB substrate was added and incubated at room temperature for 1-5 minutes (TMB Substrate, Sigma, St. Louis, Mo.). The reaction was stopped with 100 µl of 0.18M Sulfuric Acid.

The intensity of the reaction was measured at 450 nm using a microplate reader. MRP8/14 concentrations were obtained for the standard, samples, blanks, and controls as described above for determination of MRP8/14 levels). Concentration values were compared to values previously obtained by ELISA. The data confirmed that decreasing the total test time down to 1 hour does not affect standard, sample, and control values. An example of results from this 60-minute assay is listed in Table 3.

TABLE 3

Plasma AppyScore ™ value from 60-Minute Assay

| Sample ID | 60-minute AppyScore ™ | AppyGrade ™ Score |
|---|---|---|
| N-79 | 72 | 3 |
| N-84 | 42 | 3 |
| N-86 | 35 | 3 |
| N-93 | 23 | 3 |
| N-98 | 31 | 3 |
| N-64 | 12 | 1 |
| N-76 | 40 | 1 |
| N-77 | 11 | 1 |
| N-78 | 17 | 1 |
| N-80 | 9 | 1 |
| N-81 | 41 | 1 |
| N-82 | 18 | 1 |
| N-83 | 9 | 1 |
| N-85 | 11 | 1 |
| N-88 | 16 | 1 |
| N-89 | 7 | 1 |
| N-92 | 15 | 1 |
| N-95 | 9 | 1 |
| N-97 | 13 | 1 |
| N-100 | 9 | 1 |
| N-104 | 11 | 1 |
| N-106 | 8 | 1 |

Example 8

Establishment of Reference Standard Curve, AppyScore™ Value and Standard Bank

The serum reference standard was composed of appendicitis patient samples with high appendicitis histopathological grades. These selected samples were pooled and aliquots were made and stored at −80° C. A usable dilution scheme was established starting at a 1:100 dilution and continued with a serial two-fold dilution to a 1:6400 dilution. The first dilution (1:100) was assigned an arbitrary unit of 6400 and subsequent dilutions were numbered in two-fold increments down to 100 for the seventh dilution (1:6400). Two ELISA plates were run with the standard dilutions loaded across in checkerboard format in accordance with procedures described above for determining MRP8/14 concentrations. The standard curve was prepared by averaging the absorbance values and subtracting it from the blank average to obtain the corrected absorbance at 450 nm. The arbitrary units were analyzed by the transformation of units in Log10, Log2, and natural log. Each method of analysis was plotted versus the corrected absorbance (450 nm). The transformation of arbitrary units to natural log was the optimal choice for analysis of the standard curve due to the linearity and corrected absorbance values falling within a range of approximately 0.2 and 2.0. This procedure was repeated several times to determine reproducibility.

The same analysis was conducted to establish the plasma reference standard with minor changes as described below. The plasma reference standard is composed of appendicitis patient samples with high appendicitis histopathological grades. The dilution scheme started at a 1:25 dilution and continued with serial two-fold dilutions to a 1:1600 dilution. The first dilution (1:25) was assigned the arbitrary unit of 1600 and subsequent dilutions were numbered in two-fold increments down to 25 for the seventh dilution (1:1600). The transformation of arbitrary units to natural log was also the most suitable choice for analysis of the plasma standard curve. Similar to the establishment of the serum reference standard, this procedure was repeated several times to determine reproducibility of the plasma reference standard curve.

Example 9

Establishment of Sample Dilutions

The same method was conducted for both plasma and serum samples to determine the appropriate dilution for the ELISA. Samples were chosen with known appendicitis grades and were diluted as the corresponding reference standard. All standard and sample dilutions were loaded onto a plate and analyzed by ELISA as described above. Dilutions for the plasma and serum samples were chosen based on how close the sample-corrected absorbance values fell within the middle of the standard curve range of 0.2 to 2.0. The 1:100 dilution was selected for the plasma samples and the 1:200 for the serum samples.

Example 10

Curve Calibration and Creation of New Standard Banks

Samples for new reference standards were selected based on similar appendicitis histopathological grades and MRP8/14 values to those of the current reference standard. These selected samples were pooled and aliquots were made and stored at −80° C. The ELISA was used to determine validity of the new reference standard by calibrating it against the current reference standard. Two plates were assayed; one with the current and the other with the new reference standard, in accordance with the procedures described above for determining MRP8/14 concentrations. Both plates were treated alike by assaying the identical controls and samples on each to determine consistency of data between standards. This procedure was performed to obtain data for six ELISA plates. MRP8/14 values for the standard, control, and samples were obtained for all six plates as described above. The current reference standard curve values were averaged and the standard deviations, coefficient of variation, slope, correlation, maximum and minimum absorbance values determined. Sample and control values were also calculated. The same analyses were applied to the new reference standard curve values for calibration purposes. Components of the two standard curves were compared and were statistically indistinguishable (FIG. 8). Sample and control values were also statistically indistinguishable between the two standards and corresponded with values previously acquired by ELISA.

Example 11

Pilot Clinical Study Results

Heparinized plasma samples were obtained from 75 evaluable emergency room cases before final diagnoses were made. The AppyScore™ (MRP8/14) values were determined by ELISA and are listed in Tables 4 and 5. Of the 75 cases, 39 individuals were determined to not have appendicitis (Grade 1). The remaining 36 appendicitis patients were assigned an AppyGrade™ score (determined by histopathological grading). There were 6 Grade 2 cases, 23 Grade 3 cases and 7 Grade 4 cases. The average AppyScore™ values (±SEM) are illustrated in FIGS. 2 and 3. Patients diagnosed with appendicitis had an average AppyScore™ value of 87 (±12.6). One patient, N-116, had an AppyScore™ value of 1586, which is nearly 7 times higher than the next highest value in the group. As a result, the AppyScore™ value of patient N-116 was excluded from the averaging. Patients diagnosed as not having appendicitis had an average AppyScore™ value of 36 (±8.6). FIG. 2 illustrates the relationship between AppyScore™ value and severity of the appendicitis. The AppyScore™ values for Grades 1, 2, 3 and 4 are 36, 61, 84 and 125, respectively. According to this data, AppyScore™ value correlates with severity of disease.

TABLE 4

Plasma AppyScore ™ Values from Appendicitis Patients

| Sample ID | AGE | AppyScore ™ Value | AppyGrade ™ Score | Diagnosis |
|---|---|---|---|---|
| N-116 | 14 | 1586 | 4 | Appendicitis Grade 4 |
| N-130 | 17 | 237 | 4 | Appendicitis Grade 4 |
| N-91 | 8 | 210 | 4 | Appendicitis Grade 4 |
| N-57 | 53 | 101 | 4 | Appendicitis Grade 4 |
| N-150 | 44 | 100 | 4 | Appendicitis Grade 4 |
| N-135 | 12 | 77 | 4 | Appendicitis Grade 4 |
| N-145 | 35 | 26 | 4 | Appendicitis Grade 4 |
| N-90 | 25 | 381 | 3 | Appendicitis Grade 3 |
| N-103 | 17 | 185 | 3 | Appendicitis Grade 3 |
| N-133 | 35 | 136 | 3 | Appendicitis Grade 3 |
| N-119 | 13 | 121 | 3 | Appendicitis Grade 3 |
| N-141 | 33 | 116 | 3 | Appendicitis Grade 3 |
| N-79 | 30 | 93 | 3 | Appendicitis Grade 3 |
| N-115 | 20 | 86 | 3 | Appendicitis Grade 3 |
| N-111 | 19 | 81 | 3 | Appendicitis Grade 3 |
| N-84 | 25 | 81 | 3 | Appendicitis Grade 3 |
| N-86 | 28 | 80 | 3 | Appendicitis Grade 3 |
| N-148 | 52 | 72 | 3 | Appendicitis Grade 3 |
| N-108 | 46 | 65 | 3 | Appendicitis Grade 3 |
| N-55 | 12 | 63 | 3 | Appendicitis Grade 3 |
| N-98 | 12 | 55 | 3 | Appendicitis Grade 3 |
| N-71 | 37 | 46 | 3 | Appendicitis Grade 3 |
| N-75 | 14 | 44 | 3 | Appendicitis Grade 3 |
| N-149 | 17 | 39 | 3 | Appendicitis Grade 3 |
| N-93 | 40 | 38 | 3 | Appendicitis Grade 3 |
| N-127 | 11 | 36 | 3 | Appendicitis Grade 3 |
| N-53 | 23 | 29 | 3 | Appendicitis Grade 3 |
| N-73 | 19 | 27 | 3 | Appendicitis Grade 3 |
| N-51 | 9 | 25 | 3 | Appendicitis Grade 3 |
| N-94 | 36 | 21 | 3 | Appendicitis Grade 3 |
| N-118 | 46 | 178 | 2 | Appendicitis Grade 2 |
| N-56 | 14 | 74 | 2 | Appendicitis Grade 2 |
| N-128 | 17 | 54 | 2 | Appendicitis Grade 2 |
| N-68 | 13 | 27 | 2 | Appendicitis Grade 2 |
| N-67 | 16 | 20 | 2 | Appendicitis Grade 2 |
| N-49 | 13 | 11 | 2 | Appendicitis Grade 2 |

TABLE 5

Plasma AppyScore ™ Values from Nonappendicitis Patients

| Sample ID | AGE | Appyscore ™ Value | AppyGrade ™ Score | Diagnosis |
|---|---|---|---|---|
| N-65 | 47 | 234 | 1 | Ovarian Cyst |
| N-72 | 20 | 212 | 1 | Ovarian Cyst |
| N-113 | 17 | 175 | 1 | Mesenteric Adenitis |
| N-124 | 12 | 88 | 1 | Idiopathic |
| N-81 | 44 | 77 | 1 | Idiopathic |
| N-132 | 43 | 73 | 1 | Idiopathic |
| N-82 | 10 | 33 | 1 | Idiopathic |
| N-54 | 17 | 27 | 1 | Idiopathic |
| N-88 | 9 | 25 | 1 | Idiopathic |
| N-131 | 59 | 24 | 1 | Idiopathic |
| N-85 | 15 | 24 | 1 | Idiopathic |
| N-112 | 23 | 23 | 1 | Ovarian Cyst |
| N-60 | 48 | 22 | 1 | Idiopathic |
| N-101 | 48 | 22 | 1 | Idiopathic |
| N-78 | 44 | 21 | 1 | Idiopathic |
| N-105 | 20 | 21 | 1 | Idiopathic |
| N-92 | 33 | 21 | 1 | Idiopathic |
| N-146 | 18 | 21 | 1 | Idiopathic |
| N-140 | 52 | 20 | 1 | Idiopathic |
| N-59 | 30 | 19 | 1 | Ovarian Cyst |
| N-136 | 32 | 15 | 1 | Idiopathic |
| N-70 | 17 | 15 | 1 | Idiopathic |
| N-109 | 23 | 15 | 1 | Idiopathic |
| N-61 | 27 | 14 | 1 | Idiopathic |
| N-97 | 41 | 14 | 1 | Idiopathic |
| N-117 | 20 | 14 | 1 | Idiopathic |
| N-62 | 36 | 14 | 1 | Idiopathic |
| N-143 | 13 | 14 | 1 | Ovarian Cyst |
| N-83 | 44 | 13 | 1 | Idiopathic |
| N-64 | 16 | 13 | 1 | Ovarian Cyst |
| N-77 | 13 | 13 | 1 | Idiopathic |
| N-80 | 13 | 11 | 1 | Idiopathic |
| N-100 | 39 | 11 | 1 | Psychosomatic disease |
| N-89 | 25 | 11 | 1 | Ovarian Cyst |
| N-107 | 24 | 10 | 1 | Idiopathic |
| N-134 | 21 | 10 | 1 | Ovarian Cyst |
| N-142 | 27 | 8 | 1 | Ovarian Cyst |
| N-147 | 14 | 8 | 1 | Idiopathic |
| N-74 | 14 | 8 | 1 | Idiopathic |

Example 12

Characterization of Heparinized Plasma from Normal Donors

Heparinized plasma from 100 apparently healthy donors was evaluated using the AppyScore™ test. Results of those tests are shown in Table 6. The normal donor group had an average AppyScore™ value of 25 (±3.4).

TABLE 6

Plasma AppyScore ™ Values from Normal Donors

| Sample ID | Age (years) | AppyScore |
|---|---|---|
| AB-1-HP | 27 | 17 |
| AB-2-HP | 27 | 64 |
| AB-3-HP | 30 | 27 |
| AB-4-HP | 23 | 43 |
| AB-5-HP | 26 | 38 |
| AB-6-HP | 23 | 35 |
| AB-7-HP | 26 | 194 |
| AB-8-HP | 30 | 15 |
| AB-9-HP | 21 | 10 |
| AB-10-HP | 30 | 36 |
| AB-11-HP | 21 | 193 |
| AB-12-HP | 29 | 19 |

TABLE 6-continued

Plasma AppyScore™ Values from Normal Donors

| Sample ID | Age (years) | AppyScore |
|---|---|---|
| AB-13-HP | 26 | 29 |
| AB-14-HP | 28 | 25 |
| AB-15-HP | 28 | 43 |
| AB-16-HP | 19 | 18 |
| AB-17-HP | 25 | 108 |
| AB-18-HP | 28 | 82 |
| AB-19-HP | 29 | 21 |
| AB-20-HP | 26 | 7 |
| AB-21-HP | 26 | 23 |
| AB-22-HP | 29 | 54 |
| AB-23-HP | 21 | 14 |
| AB-24-HP | 30 | 11 |
| AB-25-HP | 30 | 27 |
| AB-26-HP | 25 | 16 |
| AB-27-HP | 25 | 93 |
| AB-28-HP | 28 | 93 |
| AB-29-HP | 24 | 69 |
| AB-30-HP | 29 | 89 |
| AB-31-HP | 19 | 6 |
| AB-32-HP | 21 | 17 |
| AB-33-HP | 27 | 9 |
| AB-34-HP | 27 | 8 |
| AB-35-HP | 30 | 12 |
| AB-36-HP | 27 | 114 |
| AB-37-HP | 30 | 7 |
| AB-38-HP | 29 | 16 |
| AB-39-HP | 29 | 6 |
| AB-40-HP | 25 | 72 |
| AB-41-HP | 26 | 12 |
| AB-42-HP | 30 | 19 |
| AB-43-HP | 30 | 19 |
| AB-44-HP | 27 | 35 |
| AB-45-HP | 29 | 24 |
| AB-46-HP | 19 | 12 |
| AB-47-HP | 23 | 5 |
| AB-48-HP | 23 | 8 |
| AB-49-HP | 29 | 5 |
| AB-50-HP | 22 | 12 |
| AB-51-HP | 25 | 6 |
| AB-52-HP | 30 | 9 |
| AB-53-HP | 27 | 7 |
| AB-54-HP | 22 | 12 |
| AB-55-HP | 29 | 6 |
| AB-56-HP | 25 | 8 |
| AB-57-HP | 21 | 11 |
| AB-58-HP | 30 | 7 |
| AB-59-HP | 30 | 17 |
| AB-60-HP | 22 | 6 |
| AB-61-HP | 29 | 8 |
| AB-62-HP | 27 | 8 |
| AB-63-HP | 24 | 5 |
| AB-64-HP | 21 | 10 |
| AB-65-HP | 30 | 7 |
| AB-66-HP | 21 | 8 |
| AB-67-HP | 26 | 6 |
| AB-68-HP | 21 | 6 |
| AB-69-HP | 28 | 9 |
| AB-70-HP | 22 | 7 |
| AB-71-HP | 24 | 6 |
| AB-72-HP | 27 | 10 |
| AB-73-HP | 21 | 20 |
| AB-74-HP | 23 | 12 |
| AB-75-HP | 24 | 8 |
| AB-76-HP | 23 | 7 |
| AB-77-HP | 21 | 10 |
| AB-78-HP | 21 | 9 |
| AB-79-HP | 28 | 85 |
| AB-80-HP | 26 | 38 |
| AB-81-HP | 23 | 8 |
| AB-82-HP | 22 | 7 |
| AB-83-HP | 22 | 15 |
| AB-84-HP | 26 | 7 |
| AB-85-HP | 28 | 12 |
| AB-86-HP | 23 | 32 |
| AB-87-HP | 30 | 6 |
| AB-88-HP | 21 | 5 |
| AB-89-HP | 21 | 7 |
| AB-90-HP | 22 | 9 |
| AB-91-HP | 23 | 9 |
| AB-92-HP | 28 | 5 |
| AB-93-HP | 30 | 6 |
| AB-94-HP | 22 | 15 |
| AB-95-HP | 28 | 9 |
| AB-96-HP | 23 | 12 |
| AB-97-HP | 26 | 8 |
| AB-98-HP | 25 | 7 |
| AB-99-HP | 25 | 6 |
| AB-100-HP | 24 | 8 |

Example 13

Establishment of the AppyScore™ Value Threshold Range and Triage Test Concept

After examining the AppyScore™ data two AppyScore™ threshold values were analyzed. Ninety-seven percent (97%) (35/36) of the appendicitis patients had AppyScore™ values of 20 or above. 52% (20/39) of the nonappendicitis patients had AppyScore™ values of 20 or below. 92% (33/36) of the appendicitis patients had AppyScore™ values of 25 or above. Seventy-seven percent (77%) (30/39) of the nonappendicitis patients had AppyScore™ values of 25 or below. It must be noted that the appendicitis patient, N-49 (AppyScore™ value=11), with a value below 25 was determined to have the very earliest detectable histopathological finding and was considered very close to normal. If that patient were considered normal for the purposes of threshold determination, then the threshold of 25 would result in 94% sensitivity, 77% specificity and an overall accuracy of 85%.

The AppyScore™ value can be used to identify patients that do not require further workup for appendicitis because they have been ruled out on the basis of this value. The overriding advantage of the test of this invention is that the number unnecessary costly computed tomography (CT) scans are reduced. Based on this data, the AppyScore test can be used to identify patients with appendicitis with high (92-97%) sensitivity. In this case of 75 patients in this study-using a threshold of 20-twenty patients were correctly identified as not having appendicitis and would not need further appendicitis workup. Using a threshold of 25, 30 patients would have had the diagnosis of appendicitis ruled out. Considering that a CT scan can currently cost $3000-$5000, the total cost savings on CT alone in this population of 75 patients could have been between $60,000 and $150,000, depending upon the threshold used.

We have established a blood-testing platform that has practical usefulness in an emergency room setting for cases in which lower-right-quadrant pain is associated with a suspicion of appendicitis. The level of the blood marker (MRP8/14, AppyScore™ value) is increased in patients with appendicitis. Furthermore, trend was observed in which the severity of appendicitis corresponds with the level of MRP8/14. The AppyScore™ test enables the identification patients with appendicitis and those nonappendicitis patients that do not need further appendicitis workup.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures, techniques, and embodiments, and variations respectively thereof, other than those specifically described herein can be applied to the practice of the invention as broadly disclosed herein without resort to undue experimentation. All art-known functional equivalents are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

All references throughout this application, for example publications, patents, and patent documents, are incorporated by reference herein in their entireties, as though individually incorporated by reference, to the extent each reference is at not inconsistent with the disclosure in this application.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof.

REFERENCES

Aadland E, Fagerhol M K. Faecal calprotectin: a marker of inflammation throughout the intestinal tract. Europ J Gastroenterol Hepatol 2002; 14:1

Ahlquist D A, Gilbert J A. Stool markers for colorectal screening: future considerations. Dig Dis 1996; 14(3):132-44.

Alic M. Is fecal calprotectin the next standard in inflammatory bowel disease activity tests?. [Letter] American Journal of Gastroenterology 1999; 94(11):3370-1.

Arnott I D R, Watts D, Ghosh S. Review article: is clinical remission the optimum therapeutic goal in the treatment of Crohn's disease? Aliment Pharmacol Ther 2002; 16:857.

Arredouani M S, Kasran A, Vanoirbeek J A, Berger F G, Baumann H, Ceuppens J L. 2005. Haptoglobin dampens endotoxin-induced inflammatory effects both in vitro and in vivo. Immunology. 114(2):263-71.

Aurameas et al. (1978). Scand. J Immunol., 8(7):7-23.

Berger D, Bolke E, Seidelmann M, Beger H G. Time-scale of interleukin-6, myeloid related proteins (MRP), C reactive protein (CRP), and endotoxin plasma levels during the postoperative acute phase reaction. Shock 1997; 7(6):422-6.

Berntzen H B, Endresen G K, Fagerhol M K, Spiechowicz J, Mowinckel P. Calprotectin (the L1 protein) during surgery in patients with rheumatoid arthritis. Scand J Clin Lab Invest 1991; 51(7):643-50.

Berntzen H B, Fagerhol M K, Ostensen M, Mowinckel P, Hoyeraal H M. The L1 protein as a new indicator of inflammatory activity in patients with juvenile rheumatoid arthritis. J Rheumatol 1991; 18(1):133-8.

Berntzen H B, Munthe E, Fagerhol M K. A longitudinal study of the leukocyte protein L1 as an indicator of disease activity in patients with rheumatoid arthritis. J Rheumatol 1989; 16(11):1416-20.

Berntzen H B, Munthe E, Fagerhol M K. The major leukocyte protein L1 as an indicator of inflammatory joint disease. Scand J Rheumatol 1988; Supp 76:251-6.

Berntzen H B, Olmez U, Fagerhol M K, Munthe E. The leukocyte protein L1 in plasma and synovial fluid from patients with rheumatoid arthritis and osteoarthritis. Scand J Rheumatol 1991; 20(2):74-82.

Berstad A, Arsland G, Folvik G. Relationship between intestinal permeability and calprotectin in gut lavage fluid. Scand J Gastroenterol 2000; 35(1):64-9.

Bjarnason I, Sherwood R. Fecal calprotectin: a significant step in the noninvasive assessment of intestinal inflammation. J Pediatr Gastroent Nutr 2001; 33:11.

Bjerke K, Halstensen T S, Jahnsen F, Pulford K, Brandtzaeg P. Distribution of macrophages and granulocytes expressing L1 protein (calprotectin) in human Peyer's patches compared with normal ileal lamina propria and mesenteric lymph nodes. Gut 1993; 34(10):1357-63.

Bogumil T, Rieckmann P, Kubuschok B, Felgenhauer K, Bruck W. Serum levels of macrophage-derived protein MRP8/14 are elevated in active multiple sclerosis. Neuroscience Letters 1998; 247(2-3):195-7

Bonaldo M F et al., 1996. Normalization and subtraction: Two approaches to facilitate Gene discovery. Genome Res. 6:791-806.

Brandtzaeg P, Dale I, Fagerhol M K. Distribution of a formalin-resistant myelomonocytic antigen (L1) in human tissues. I. Comparison with other leukocyte markers by paired immunofluorescence and immunoenzyme staining. Am J Clin Pathol 1987; 87(6):681-99.

Brandtzaeg P, Dale I, Fagerhol M K. Distribution of a formalin-resistant myelomonocytic antigen (L1) in human tissues. II. Normal and aberrant occurrence in various epithelia. Am J Clin Pathol 1987; 87(6):700-7.

Brandtzaeg P, Dale I, Gabrielsen T O. The leukocyte protein L1 (calprotectin): usefulness as an immunohistochemical marker antigen and putative biological function. Histopathol 1992; 21(2):191-6.

Brun J G, Cuida M, Jacobsen H, Kloster R, Johannesen A C, Hoyeraal H M, Jonsson R. Sjogren's syndrome in inflammatory rheumatic diseases: analysis of the leukocyte protein calprotectin in plasma and saliva. Scand J Rheumatol 1994; 23(3):114-8.

Brun J G, Haga H J, Boe E, Kallay I, Lekven C, Berntzen H B, Fagerhol M K. Calprotectin in patients with rheumatoid arthritis: relation to clinical and laboratory variables of disease activity. J Rheumatol 1992; 19(6):859-62.

Brydon W G, Campbell S S, Anderson N A, Wilson R G, Ghosh S. Faecal calprotectin levels and colorectal neoplasia. Gut 2001; 48(4):579-80.

Bunn S K, Bisset W M, Main M J, Golden B E. Fecal calprotectin as a measure of disease activity in childhood inflammatory bowel disease. J Pediatr Gastroenterol Nutr 2001; 32(2):171-7

Bunn S K, Bisset W M, Main M J C, Gray E S, Olson S, Golden B E. Fecal calprotectin: Validation as a noninvasive measure of bowel inflammation in childhood inflammatory bowel disease. J Pediatr Gastroenterol Nutr 2001; 33:11.

Burkhardt K, Radespiel-Troger M, Rupprecht H D, Goppelt-Struebe M, Riess R, Renders L, Hauser I A, and U Kunzendorf 2001. An increase in myeloid-related protein serum levels precedes acute renal allograft rejection. J Am Soc Nephrol 12:1947-57.

Clark B R, Kelly S E, Fleming S. Calgranulin expression and association with the keratinocyte cytoskeleton. J Pathol 1990; 160(1):25-30

Dale I, Brandtzaeg P, Fagerhol M K, Scott H. Distribution of a new myelomonocytic antigen (L1) in human peripheral blood leukocytes. Immunofluorescence and immunoperoxidase staining features in comparison with lysozyme and lactoferrin. Am J Clin Pathol 1985; 84(1):24-34.

Dale I, Brandtzaeg P. Expression of the epithelial L1 antigen as an immunohistochemical marker of squamous cell carcinoma of the lung. Histopathol 1989; 14(5):493-502.

Dale I. Plasma levels of the calcium-binding L1 leukocyte protein: standardization of blood collection and evaluation of reference intervals in healthy controls. Scand J Clin Lab Invest 1990; 50(8) :837-41.

Deichmann, M., Polychronidis, M., Wacker, J., Thome, M. & Naher, H., 2001. The protein phosphatase 2A subunit Bg gene is identified to be differentially expressed in malignant melanomas by subtractive suppression hybridization. Melanoma Research 2001(11):1-9. DeLuca (1982). "Immunofluorescence Analysis," Antibody As a Tool, Marchalonis et al., Eds., John Wiley & Sons, Ltd., pp. 189-231.

Dobryszycka W. 1997. Biological functions of haptoglobin--new pieces to an old puzzle. Eur J Clin Chem Clin Biochem 35(9):647-54.

Eversole L R, Miyasaki K T, Christensen R E. Keratinocyte expression of calprotectin in oral inflammatory mucosal diseases. J Oral Pathol Med 1993; 22(7):303-7.

Eversole L R, Miyasaki K T, Christensen R E. The distribution of the antimicrobial protein, calprotectin, in normal oral keratinocytes. Arch Oral Biol 1992; 37(11):963-8.

Fagerhol M K, Andersson K B, Naess-Andresen C F, Brandtzaeg P, Dale I. Calprotectin (The L1 Leukocyte Protein) In: V L Smith & J R Dedman (Eds): Stimulus Response Coupling. The Role of Intracellular Calcium-Binding Proteins, CRC Press, Boca Raton, Fla., USA, 1990, pp. 187-210.

Fagerhol M K. Calprotectin, a faecal marker of organic gastrointestinal abnormality. Lancet 2000; 356(9244):1783-4.

Flum D R et al., 2001. Has misdiagnosis of appendicitis decreased over time? A population-based analysis. JAMA 286 (14):1748-1753.

Foell, D. et al. "Neutrophil derived human S100A12 (EN-RAGE) is strongly expressed during chronic active inflammatory bowel disease, Gut 2003, 52:847-853.

Fosse E, Moen O, Johnson E, Semb G, Brockmeier V, Mollnes T E, Fagerhol M K, Venge P. Reduced complement and granulocyte activation with heparin-coated cardiopulmonary bypass. Annals of Thoracic Surgery 1994; 58(2):472-7.

Frosch M, Strey A, Vogl T, Wulffraat N M, Kuis W, Sunderkotter C, Harms E, Sorg C, and J Roth 2000. Myeloid-related proteins 8 and 14 are specifically secreted during interaction of phagocytes and activated endothelium and are useful markers for monitoring disease activity in pauciarticular-onset juvenile rheumatoid arthritis. Arthritis Rheum 43:628-37.

Gabrielsen TO, Brandtzaeg P, Hoel PS, Dale I. Epithelial distribution of a myelomonocytic antigen L1 in relation to cutaneous malignancies and melanocytic naevi. BrJ Dermatol 1988; 118(1):59-67.

Gabrielsen T O, Dale I, Brandtzaeg P, Hoel P S, Fagerhol M K, Larsen T E, Thune P O. Epidermal and dermal distribution of a myelomonocytic antigen (L1) shared by epithelial cells in various inflammatory skin diseases. J Am Acad Dermatol 1986; 15(2 Pt 1):173-9.

Galfre et al. (1981), Meth. Enzymol., 73:3-46.

Garred P, Fosse E, Fagerhol M K, Videm V, Mollnes T E. Calprotectin and complement activation during major operations with or without cardiopulmonary bypass. Annals of Thoracic Surgery 1993; 55(3):694-9.

Gasché, C., 2005. Laboratory Tests-What Do They Tell Us?, Falk Symposium Abstract, June 17-18, 2005, Munich, Germany.

Gaya D R, Mackenzie J F. Faecal calprotectin: a bright future for assessing disease activity in Crohn's disease. Q J Med 2002; 95:557 (editorial).

Gilbert J A, Ahlquist D A, Mahoney D W, Zinsmeister A R, Rubin J, Ellefson R D. Fecal marker variability in colorectal cancer: calprotectin versus hemoglobin. Scand J Gastroenterol 1996; 31(10):1001-5.

Golden B E, Clohessy P A, Russell G, Fagerhol M K. Calprotectin as a marker of inflammation in cystic fibrosis. Archives of Disease in Childhood 1996; 74(2):136-9.

Haga H J, Brun J G, Berntzen H B, Cervera R, Khamashta M, Hughes G R. Calprotectin in patients with systemic lupus erythematosus: relation to clinical and laboratory parameters of disease activity. Lupus 1993; 2(1):47-50.

Haidekker M A, et al., 2002. A novel approach to blood plasma viscosity measurement using fluorescent molecular rotors. Am J Physiol Heart Circ Physio 282:H1609-H1614.

Hammer H B, Kvien T K, Glennas A, Melby K. A longitudinal study of calprotectin as an inflammatory marker in patients with reactive arthritis. Clin Exp Rheumatol 1995; 13(1):59-64.

Hanai H, Takeuchi K, Iida T, Arai H, Kanaoka K, Iwasaki T, Nakamura A, Hosoda Y, Shirai N, Hirasawa K, Takahira K, Kataoka H, Sano M, Osawa M, Sugimoto S. Clinical significance of faecal calprotectin levels in patients with ulcerative colitis. Nippon Shokakibyo Gakkai Zasshi 2003; 100:21.

Harkness J., 1963. A new method for the measurement of plasma viscosity. Lancet 2:280 -281.

Harlow et al. (1988). Antibodies, Cold Spring Harbor Laboratory. Hessian, P. A. and Fisher, P. A., 2001, "The heterodimeric complex of MRP-8 (S100A8) and MRP-14 (S100A9): Antibody recognition, epitope definition and the implications for structure," Eur J. Biochem 268:353-363.

Hetland G, Berntzen H B, Fagerhol M K. Levels of calprotectin (leukocyte L1 protein) during apheresis. Scand J Clin Lab Invest 1992; 52(6):479-82.

Homann C, Garred P, Graudal N, Hasselqvist P, Christiansen M, Fagerhol M K, Thomsen A C. Plasma calprotectin: a new prognostic marker of survival in alcohol-induced cirrhosis. Hepatol 1995; 21(4):979-85.

Hsieh H L, Schafer B W, Weigle B, and C W Heizmann 2004 S100 protein translocation in response to extracellular S100 is mediated by receptor for advanced glycation end-products in human endothelial cells. Biochem Biophys Res Commun 316:949-59.

Hycult Biotechnology b.v., ELISA Test Kit for Human Calprotectin information sheet, Catalog No. HK325.

Hycult Biotechnology b.v., Monoclonal Antibody to Human S100A8/A9 (MRP-8/MRP-14), calprotectin Clone 27E10 information sheet, Catalog No. HM2156.

Ikemoto, M., et al. 2003. New ELISA System for Myeloid-related Protein Complex (MRP8/14) and its Clinical Significance as a Sensitive Marker for Inflammatory Responses Associated with Transplant Rejection, Clin. Chem. 49:594-600.

Johne B, Fagerhol M K, Lyberg T, Prydz H, Brandtzaeg P, Naess-Andresen C F, Dale I. Functional and clinical aspects of the myelomonocyte protein calprotectin. Molecular Pathology 1997; 50(3):113-23.

Johne B, Kronborg O, Ton H I, Kristinsson J, Fuglerud P. A new fecal calprotectin test for colorectal neoplasia. Clinical results and comparison with previous method. Scand J Gastroenterol 2001; 36(3):291-6.

Katnik et al, 1989. Monoclonal Antibodies Against Human Haptoglobin. Hybridoma 8: (5):551 -560.

Kelly S E, Hunter J A, Jones D B, Clark B R, Fleming S. Morphological evidence for calcium-dependent association of calgranulin with the epidermal cytoskeleton in inflammatory dermatoses. Br J Dermatol 1991; 124(5): 403-9.

Kelly S E, Jones D B, Fleming S. Calgranulin expression in inflammatory dermatoses. J Pathol 1989; 159(1):17-21.

Kerkhoff C, Klempt M, Sorg C. Novel insights into structure and function of MRP8 (S100A8) and MRP14 (S100A9). Biochimica et Biophysica Acta 1998; 1448(2):200-11.

Kjeldsen-Kragh J, Mellbye O J, Haugen M, Mollnes T E, Hammer H B, Sioud M, Forre O. Changes in laboratory variables in rheumatoid arthritis patients during a trial of fasting and one-year vegetarian diet. Scand J Rheumatol 1995; 24(2):85-93.

Koike T, Kondo K, Makita T, Kajiyama K, Yoshida T, Morikawa M. Intracellular localization of migration inhibitory factor-related protein (MRP) and detection of cell surface MRP binding sites on human leukemia cell lines. J Biochem 1998; 123(6):1079-87.

Kristinsson J, Armbruster C H, Ugstad M, Kriwanek S, Nygaard K, Ton H, Fuglerud P. Fecal excretion of calprotectin in colorectal cancer; relationship to tumor characteristics. Scand J Gastroenterol 2001; 36(2):202-7.

Kristinsson J, Roseth A, Fagerhol M K, Aadland E, Schjonsby H, Bormer O P, Raknerud N, Nygaard K. Fecal calprotectin concentration in patients with colorectal carcinoma. Diseases of the Colon & Rectum 1998; 41(3):316-21.

Kronborg O, Ugstad M, Fuglerud P, Johne B, Hardcastle J, Scholefield J H, Vellacott K, Moshakis V, Reynolds J R. Faecal calprotectin levels in a high risk population for colorectal neoplasia. Gut 2000; 46(6):795-800.

Kumar, R. K., et al. 2001. Dimeric S100A8 in human neutrophils is diminished after phagocytosis, J. Leukoc. Biol. 70(1):59-64.

Limburg P J, Ahlquist D A, Sandborn W J, Mahoney D W, Devens M E, Harrington J J and A R Zinsmeister 2000. Fecal calprotectin levels predict colorectal inflammation among patients with chronic diarrhea referred for colonoscopy. Am J Gastroenterol, 10:2831-7.

Limburg P J. Ahlquist D A. Sandborn W J. Mahoney D W. Devens M E. Harrington J J. Zinsmeister A R. Fecal calprotectin levels predict colorectal inflammation among patients with chronic diarrhea referred for colonoscopy. American Journal of Gastroenterology 2000; 95(10):2831-7.

Longbottom D, Sallenave J M, van Heyningen V. Subunit structure of calgranulins A and B obtained from sputum, plasma, granulocytes and cultured epithelial cells. Biochimica et Biophysica Acta 1992; 11 20(2):215-22.

Lugering N, Stoll R, Schmid K W, Kucharzik T, Stein H, Burmeister G, Sorg C, Domschke W. The myeloic related protein MRP8/14 (27E10 antigen)-usefulness as a potential marker for disease activity in ulcerative colitis and putative biological function. Europ J Clin Invest 1995; 25(9):659-64.

Meling T R. Aabakken L. Roseth A. Osnes M. Faecal calprotectin shedding after short-term treatment with non-steroidal anti-inflammatory drugs. Scandinavian Journal of Gastroenterology 1996; 31 (4):339-44.

Moen O, Fosse E, Braten J, Andersson C, Fagerhol M K, Venge P, Hogasen K, Mollnes T E. Roller and centrifugal pumps compared in vitro with regard to haemolysis, granulocyte and complement activation. Perfusion 1994; 9(2): 109-17.

Muller F, Froland S S, Aukrust P, Fagerhol M K. Elevated serum calprotectin levels in HIV-infected patients: the calprotectin response during ZDV treatment is associated with clinical events. J Acq Immune Defic Syndr 1994; 7(9):931-9.

Muller, F., et al. 1994. Elevated serum calprotectin levels in HIV-infected patients: the calprotectin response during ZDV treatment is associated with clinical events, J. Acqui. Immune Defic. Syndr. 7(9):931-939.

Neary, Walter, 2001. Press Release from University of Washington, Misdiagnosis of appendicitis continues despite new tools.

Olafsdottir E, Aksnes L, Fluge G, Berstad A. Faecal calprotectin in infants with infantile colic, healthy infants, children with inflammatory bowel disease, children with recurrent abdominal pain and healthy children. Acta Paediatr 2002; 91:45.

Pekna M, Borowiec J, Fagerhol M K, Venge P, Thelin S. Biocompatibility of heparin-coated circuits used in cardiopulmonary bypass. Scand J Thorac Cardiovasc Surg 1994; 28(1):5-11.

Power, C. et al, 2005. Raised faecal calprotectin levels in patients presenting with right iliac fossa pain warrant mandatory laparoscopy: a non-invasive predictor of acute appendicitis, Thieme connect, Endoscopy 37:DOI: 10.1055/2-2005-868524.

Power, C., et al. 2004, Irish Society of Gastroenterology Winter Meeting Program Oral Presentation Raised Faecal Calprotectin Levels in Patients Presenting with Right Iliac Fossa Pain Warrant Mandatory Laparoscopy: A Non-invasive Predictor of Acute Appendicitis.

Robinson MJ, Tessier P, Poulsom R, and N. Hogg 2002 The S100 family heterodimer, MRP8/14, binds with high affinity to heparin and heparan sulfate glycosaminoglycans on endothelial cells. J Biol Chem. 277:3658-65.

Rodwell et al. (1984). Biotech., 3:889-894.

Roseth A G, Aadland E, Grzyb K. Normalization of faecal calprotectin: a predictor of mucosal healing in patients with inflammatory bowel disease. Scand J Gastroenterol. 2004 October;39(10):1017-20.

Roseth A G, Fagerhol M K, Aadland E, Schjonsby H. Assessment of the neutrophil dominating protein calprotectin in feces. A methodologic study. Scand J Gastroenterol 1992; 27(9):793-8.

Roseth A G, Kristinsson J, Fagerhol M K, Schjonsby H, Aadland E, Nygaard K, Roald B. Faecal calprotectin: a novel test for the diagnosis of colorectal cancer? Scand J Gastroenterol 1993; 28(12):1073-6.

Roseth A G. Aadland E. Jahnsen J. Raknerud N. Assessment of disease activity in ulcerative colitis by faecal calprotectin, a novel granulocyte marker protein. Digestion 1997; 58(2):176-80.

Roseth A G. Fagerhol M K. Aadland E. Schjonsby H. Assessment of the neutrophil dominating protein calprotectin in feces. A methodologic study. Scandinavian Journal of Gastroenterology 1992; 27(9):793-8.

Roseth A G. Schmidt P N. Fagerhol M K. Correlation between faecal excretion of indium-111-labelled granulocytes and calprotectin, a granulocyte marker protein, in patients with inflammatory bowel disease. Scandinavian Journal of Gastroenterology 1999; 34(1):50-4.

Ryckman C, Vandal K, Rouleau P, Talbot M, and P A Tessier 2003 Proinflammatory activities of S100: proteins S100A8, S100A9, and S100A8/A9 induce neutrophil chemotaxis and adhesion. J Immunol. 170:3233-42.

Saintigny G, Schmidt R, Shroot B, Juhlin L, Reichert U, Michel S. Differential expression of calgranulin A and B in various epithelial cell lines and reconstructed epidermis. J Invest Dermatol 1992; 99(5):639-44.

Sander J, Fagerhol M K, Bakken J S, Dale I. Plasma levels of the leucocyte L1 protein in febrile conditions: relation to aetiology, number of leucocytes in blood, blood sedimentation reaction and C-reactive protein. Scand J Clin Lab Invest 1984; 44(4):357-62.

Semb A G, Gabrielsen T O, Halstensen T S, Fagerhol M K, Brandtzaeg P, Vaage J. Cardiac surgery and distribution of the leukocyte L1 protein-calprotectin. Europ J Cardio-Thoracic Surgery 1991; 5(7):363-7.

Shanahan F. Inflammatory bowel disease: immunodiagnostics, immunotherapeutics, and ecotherapeutics. Gastroenterol 2001; 120:622.

Stockley R A, Dale I, Hill S L, Fagerhol M K. Relationship of neutrophil cytoplasmic protein (L1) to acute and chronic lung disease. Scand J Clin Lab Invest 1984; 44(7):629-34.

Striz, I. and I. Trebichavsky 2004. Calprotectin—a Pleiotropic Molecule in Acute and Chronic Inflammation. Physiol Res. 53:245-253.

Thomas P. Rihani H. Roseth A. Sigthorsson G. Price A. Nicholls R J. Bjarnason I. Assessment of ileal pouch inflammation by single-stool calprotectin assay. Diseases of the Colon & Rectum 2000; 43(2):214-20.

Tibble J, Sigthorssorn G, Foster R, Fagerhol M K, Bjarnason I. Faecal calprotectin and faecal occult blood tests in the diagnosis of colorectal carcinoma and adenoma. Gut 2001; 49:402.

Tibble J. Teahon K. Thjodleifsson B. Roseth A. Sigthorsson G. Bridger S. Foster R. Sherwood R. Fagerhol M. Bjarnason I. A simple method for assessing intestinal inflammation in Crohn's disease. Gut 2000; 47(4):506-13.

Tibble J A, Bjarnason I. Department of Medicine, Guy's, King's, St Thomas's Medical School, Bessemer Road, London SE5 9PJ, UK.Non-invasive investigation of flammatory bowel disease.

Tibble J A, Bjarnason I. Department of Medicine, Guy's, King's, St. Thomas's Medical School, London, UK. Fecal-calprotectin as an index of intestinal inflammation.

Tibble J A, Bjarnason I. Markers of intestinal inflammation and predictors of clinical relapse in patients with quiescent IBD. Medscape Gastroenterol 2001; 3 (2).

Tibble J A. Sigthorsson G. Bridger S. Fagerhol M K. Bjarnason I. Surrogate markers of intestinal inflammation are predictive of relapse in patients with inflammatory bowel disease. [Journal Article] Gastroenterology 2000; 119(1): 15-22.

Tibble J A. Sigthorsson G. Foster R. Scott D. Fagerhol M K. Roseth A. Bjarnason I. High prevalence of NSAID enteropathy as shown by a simple faecal test. Gut 1999; 45(3): 362-6.

Ton H. Brandsnes. Dale S. Holtlund J. Skuibina E. Schjonsby H. Johne B. Improved assay for fecal calprotectin. Clinica Chimica Acta 2000; 292(1 -2):41 -54.

Tungekar M F, Heryet A, Gatter K C. The L1 antigen and squamous metaplasia in the bladder. Histopathol 1991; 19(3):245-50.

U.S. Pat. No.4,493,795, Nestor, Jr., et al., Jan. 15, 1985, Synthetic peptide sequences useful in biological and pharmaceutical applications and methods of manufacture.

U.S. Pat. No. 5,350,687, Odink, et al., Sep. 27,1994, Antibodies which bind to novel lymphokine related peptides.

U.S. Pat. No. 5,455,160, Fagerhol, et al., Diagnostic test and kit for disease disorders in the digestive system.

U.S. Pat. No. 5,552,295, Stanker, et al., Sep. 3,1996, Monoclonal antibodies to bovine haptoglobin and methods for detecting serum haptoglobin levels.

U.S. Pat. No.6,451,550, Eckersall, Sep. 17, 2002, Haptoglobin assay. U.S. Patent Publication No. 20030224452, Colgin, et al., Pregnancy Detection.

Wilkinson M M, Busuttil A, Hayward C, Brock D J, Dorin J R, Van Heyningen V. Expression pattern of two related cystic fibrosis-associated calcium-binding proteins in normal and abnormal tissues. J Cell Science 1988; 91 ( Pt 2):221-30.

Ye B, Cramer D W, Skates S J, Gygi S P, Pratomo V, Fu L, Horick N K, Licklider L J, Schorge J O, Berkowitz R S, Mok S C. 2003 Haptoglobin-alpha subunit as potential serum biomarker in ovarian cancer: identification and characterization using proteomic profiling and mass spectrometry. Clin Cancer Res 9(8):2904-11.

Yerly S, Bouvier M, Rougemont A, Srivastava I, Perrin L H. 1990. Development of a haptoglobin ELISA. Its use as an indicator for malaria. Acta Trop. 1990 47(4):237-44.

The invention claimed is:

1. A method for scoring the severity of appendicitis of a patient suspected of suffering from appendicitis who is not known to have an interfering condition associated with the presence of elevated MRP-8/14 protein in blood, serum or plasma of said patient, said interfering condition being selected from the group consisting of recent allograft; septicemia; meningitis; pneumonia; tuberculosis; rheumatoid arthritis; gastrointestinal cancer; inflammatory bowel disease; skin cancer, periodontitis, preeclampsia, and AIDS, said method comprising:
- testing a sample of blood, serum, or plasma from said patient for the quantity of MRP8/14 in said sample;
- comparing the quantity of MRP8/14 in said sample with the quantity of MRP8/14 in one or more standard samples, wherein the standard sample(s) contain quantity(ies) of MRP8/14 previously correlated with one or more grade scores for appendicitis severity; and
- assigning to the severity of appendicitis in said patient the grade score of the standard sample that has the quantity of MRP8/14 closest to the quantity of MRP8/14 present in the sample from the patient.

2. The method of claim 1 wherein the grade scores for appendicitis severity correspond to histological condition patient tissue as follows:

| | |
|---|---|
| Grade 1 | No identifiable inflammation in appendix tissue; |
| Grade 2 | Inflammation extending through the mucosa and into the submucosa of the appendix |
| Grade 3 | Inflammation extends past the submucosa into the muscular levels of the appendix |
| Grade 4 | All layers of the appendix, including the serosa, inflamed, and perforation identified. |

3. The method of claim 1 wherein said sample from the patient is a blood sample.

4. The method of claim 1 wherein said sample from the patient is a serum sample.

5. The method of claim 1 wherein the sample from the patient is a plasma sample.

6. The method of claim 1 wherein the quantity of MRP8/14 in at least one standard sample is compared with the quantity of MRP8/14 in the sample from the patient.

7. The method of claim 1 wherein the quantities of MRP8/14 in a plurality of standard samples are compared with the quantity of MRP8/14 in the sample from the patient.

8. The method of claim 1 wherein each standard sample is from an individual patient having appendicitis of a known grade.

9. The method of claim 1 wherein each standard sample comprises pooled samples from individual patients having appendicitis of a single known grade.

10. The method of claim 1 wherein each standard sample is prepared by adding to a suitable carrier a predetermined amount of MRP8/14 corresponding to an amount present in patients having appendicitis of a single known grade.

11. The method of claim 1 wherein the quantity of MRP8/14 in the sample from said patient is compared with a compilation of data representing quantities of MRP8/14 present in standard samples from patients having known appendicitis grades, the quantity of MRP8/14 in each said standard sample being correlated with the appendicitis grade of the patient from which it was taken.

12. The method of claim 11 wherein said data is expressed in assigned units mathematically related to absolute quantities of MRP8/14 in said samples.

13. The method of claim 2 wherein the sample from said patient is a plasma sample, the quantity of MRP8/14 in the sample from said patient is compared with a compilation of data representing quantities of MRP8/14 present in standard plasma samples from patients having known appendicitis grades based on their tissue histology, the quantity of MRP8/14 in each said standard sample being correlated with the appendicitis grade of the patient from which it was taken, and wherein said data is expressed in assigned units mathematically related to absolute quantities of MRP8/14 present in said standard samples, and wherein the quantity of MRP8/14 in said sample from said patient is assigned a score expressed in said units corresponding to the absolute quantity of MRP8/14 present in said sample.

14. The method of claim 13 wherein when a sample from a patient has a quantity of MRP8/14 greater than about 20-25 expressed in said units, this result indicates the patient has appendicitis.

15. The method of claim 11 wherein said data is present in a computer processor and said comparison is made by a method comprising inputting data representing the quantity of MRP8/14 in the sample from said patient into said computer processor.

16. The method of claim 15 wherein the data representing the quantity of MRP8/14 in the sample from the patient is generated by an automated system comprising detection means for detecting binding of MRP8/14 in the sample with an antibody to MRP8/14.

17. The method of claim 16 wherein said automated system is part of an automated blood testing system also comprising automated means for testing other blood components.

18. The method of claim 1 wherein determining the quantity and presence of MRP8/14 in the sample from a patient is done by a method including determining the amount of binding of MRP8/14 in said sample to an antibody or antibodies to MRP8/14.

19. The method of claim 18 wherein the amount of binding to MRP8/14 is determined by determining the amount of binding of MRP8/14 to a monoclonal antibody.

20. The method of claim 19 wherein the monoclonal antibody to MRP8/14 is 27e10.

21. The method of claim 18 wherein the amount of binding to MRP8/14 is determined by determining the amount of binding of MRP8/14 to a polyclonal antibody.

22. The method of claim 18 wherein an antibody to MRP8/14 is an antibody generated to an amino acid sequence selected from the group consisting of

```
                                              [SEQ ID NO: 1]
MLTELEKALNSIIDVYHKYSLIKGNFHAVYRDDLKKLLETECPQYIRKKG

ADVWFKELDINTDGAVNFQEFLILVIKMGVAAHKKSHEESHKE,
and/or

[SEQ ID NO: 2]
MTCKMSQLERNIETIINTFHQYSVKLGHPDTLNQGEFKELVRKDLQNFLK

KENKNEKVIEHIMEDLDTNADKQLSFEEFIMLMARLTWASHEKMHEGDEG

PGHHHKPGLGEGTP.
```

23. The method of claim 1 wherein at least one additional protein in said sample from said patient is tested for the presence of a factor correlated with the severity of appendicitis.

24. The method of claim 23 wherein said additional protein is haptoglobin.

* * * * *